United States Patent
Choi et al.

(10) Patent No.: US 10,533,189 B2
(45) Date of Patent: Jan. 14, 2020

(54) HIGHLY SPECIFIC DELIVERY OF POLYNUCLEOTIDES TO THE CELL NUCLEUS VIA COMPRESSION

(71) Applicant: THE CHINESE UNIVERSITY OF HONG KONG, Hong Kong (CN)

(72) Inventors: Chung Hang Jonathan Choi, Hong Kong (CN); Zhong Chen, Zhuhai (CN); Lei Zhang, Yangzhou (CN); Huize Li, Bozhou (CN)

(73) Assignee: THE CHINESE UNIVERSITY OF HONG KONG, Hong Kong (CN)

( * ) Notice: Subject to any disclaimer, the term of this patent is extended or adjusted under 35 U.S.C. 154(b) by 170 days.

(21) Appl. No.: 15/708,810

(22) Filed: Sep. 19, 2017

(65) Prior Publication Data
US 2018/0080050 A1    Mar. 22, 2018

Related U.S. Application Data

(60) Provisional application No. 62/397,173, filed on Sep. 20, 2016.

(51) Int. Cl.
*C12N 15/11* (2006.01)
*C12N 15/87* (2006.01)
*C12N 15/113* (2010.01)
*A61K 48/00* (2006.01)

(52) U.S. Cl.
CPC ............ *C12N 15/87* (2013.01); *C12N 15/113* (2013.01); *A61K 48/00* (2013.01); *C12N 2310/11* (2013.01); *C12N 2320/32* (2013.01)

(58) Field of Classification Search
None
See application file for complete search history.

(56) References Cited

U.S. PATENT DOCUMENTS 5,922,687 A * 7/1999 Mann ................. A61M 5/1452
435/440

FOREIGN PATENT DOCUMENTS

WO    WO-03/012039 A2    2/2003

OTHER PUBLICATIONS

Phair, Robert D. et al., High mobility of proteins in the mammalian cell nucleus, Letters to Nature, Apr. 6, 2000, 404(6778):604-609, Macmillan Magazines Ltd.
Boisvert, François-Michel et al., The multifunctional nucleolus, Nature Reviews Molecular Cell Biology, Jul. 2007, 8(7):574-585, Nature Publishing Group.
Hornung, Veit et al., Intracellular DNA recognition, Nature Reviews Immunology, Feb. 2010, 10:123-130, Macmillan Publishers Limited.
Luo, Dan et al., Synthetic DNA delivery systems, Nature Biotechnology, Jan. 2000, 18:33-37, Nature America Inc.
Torchilin, Vladimir P., Recent Approaches to Intracellular Delivery of Drugs and DNA and Organelle Targeting, Annual Review of Biomedical Engineering, 2006, 8:343-375, Annual Reviews.
Potter, Huntington et al., Enhancer-dependent expression of human K immunoglobulin genes introduced into mouse pre-B lymphocytes by electroporation, Proceedings of the National Academy of Sciences of the United States of America, Nov. 1984, 81(22):7161-7165.
Felgner, Philip L. et al., Lipofection: A highly efficient, lipid-mediated DNA-transfection procedure, Proceedings of the National Academy of Sciences of the United States of America, Nov. 1987, 84(21):7413-7417.
Boussif, Otmane et al., A versatile vector for gene and oligonucleotide transfer into cells in culture and in vivo: Polyethylenimine, Proceedings of the National Academy of Sciences of the United States of America, Aug. 1995, 92(16):7297-7301.
Suh, Junghae et al., Efficient active transport of gene nanocarriers to the cell nucleus, Proceedings of the National Academy of Sciences of the United States of America, Apr. 1, 2003, 100(7):3878-3882.
Crystal, Ronald G. et al., Transfer of Genes to Humans: Early Lessons and Obstacles to Success, Science, Oct. 20, 1995, 270(5235):404-410.
Tripathy, Sandeep K. et al., Immune responses to transgene-encoded proteins limit the stability of gene expression after injection of replication-defective adenovirus vectors, Nature Medicine, May 1996, 2(5):545-550, Nature Publishing Group.
Leonetti, Jean Paul et al., Intracellular distribution of microinjected antisense oligonucleotides, Proceedings of the National Academy of Sciences of the United States of America, Apr. 1991, 88(7):2702-2706.
Mikszta, John A. et al., Improved genetic immunization via micromechanical disruption of skin-barrier function and targeted epidermal delivery, Nature Medicine, Apr. 2002, 8(4):415-419, Nature Publishing Group.
Brandén, Lars J. et al., A peptide nucleic acid-nuclear localization signal fusion that mediates nuclear transport of DNA, Nature Biotechnology, Aug. 1999, 17:784-787, Nature America Inc.
Zanta, Maria Antonietta et al., Gene delivery: A single nuclear localization signal peptide is sufficient to carry DNA to the cell nucleus, Proceedings of the National Academy of Sciences of the United States of America, Jan. 1999, 96(1):91-96.
Dam, Duncan Hieu M. et al., Direct Observation of Nanoparticle-Cancer Cell Nucleus Interactions, ACS Nano, 2012, 6(4):3318-3326, American Chemical Society.

(Continued)

*Primary Examiner* — Ekaterina Poliakova-Georgantas
(74) *Attorney, Agent, or Firm* — Saliwanchik, Lloyd & Eisenschenk

(57) ABSTRACT

The subject invention pertains to delivering a polynucleotide into a target cell, particularly, into the nucleus of the target cell. The method comprises the steps of contacting the polynucleotide with the cell and applying pressure on the polynucleotide and the cell in a manner that forces the polynucleotide into the cell. The pressure can be between about 0.1 Pa to about 50 Pa; whereas, the polynucleotide is contacted with the cell at a concentration of between about 0.1 μM and about 100 μM. The method can be practiced for cells in culture or cells in vivo.

19 Claims, 17 Drawing Sheets

Specification includes a Sequence Listing.

(56) References Cited

OTHER PUBLICATIONS

O'Brien, John A. et al., Biolistic transfection of neuronal cultures using a hand-held gene gun, Nature Protocols, 2006, 1(2):977-981, Nature Publishing Group.

McAllister, Devin V. et al., Microfabricated Microneedles for Gene and Drug Delivery, Annual Review of Biomedical Engineering, 2000, 2:289-313, Annual Reviews.

Mann, Michael J. et al., Pressure-mediated oligonucleotide transfection of rat and human cardiovascular tissues, Proceedings of the National Academy of Sciences of the United States of America, May 1999, 96(11):6411-6416.

Yao, Yifei et al., Effects of oxidative stress-induced changes in the actin cytoskeletal structure on myoblast damage under compressive stress: confocal-based cell-specific finite element analysis, Biomech Model Mechanobiol, 2016, 15(6):1495-1508, Springer-Verlag Berlin Heidelberg.

Tse, Janet M. et al., Mechanical compression drives cancer cells toward invasive phenotype, Proceedings of the National Academy of Sciences of the United States of America, Jan. 17, 2012, 109(3):911-916.

Politz, Joan C. et al., Characterization of hybridization between synthetic oligodeoxynucleotides and RNA in living cells, Nucleic Acids Research, 1995, 23(24):4946-4953, Oxford University Press.

Stein, C. A. et al., Efficient gene silencing by delivery of locked nucleic acid antisense oligonucleotides, unassisted by transfection reagents, Nucleic Acids Research, 2010, 38(1):e3, Oxford University Press.

Rosi, Nathaniel L. et al., Oligonucleotide-Modified Gold Nanoparticles for Intracellular Gene Regulation, Science, May 19, 2006, 312(5776):1027-1030, American Association for the Advancement of Science.

Chiu, Ya-Lin et al., RNAi in Human Cells: Basic Structural and Functional Features of Small Interfering RNA, Molecular Cell, Sep. 2002, 10(3):549-561, Cell Press.

Czauderna, Frank et al., Structural variations and stabilising modifications of synthetic siRNAs in mammalian cells, Nucleic Acids Research, 2003, 31(11):2705-2716, Oxford University Press.

Morrissey, David V. et al., Potent and persistent in vivo anti-HBV activity of chemically modified siRNAs, Nature Biotechnology, Aug. 2005, 23(8):1002-1007, Nature Publishing Group.

Soutschek, Jürgen et al., Therapeutic silencing of an endogenous gene by systemic administration of modified siRNAs, Nature, Nov. 11, 2004, 432(7014)1 73-178, Nature Publishing Group.

Stewart, Martin P. et al., In vitro and ex vivo strategies for intracellular delivery, Nature, Oct. 13, 2016, 538:183-192, Macmillan Publishers Limited, part of Springer Nature.

Han, X. et al., "CRISPR-Cas9 delivery to hard-to-transfect cells via membrane deformation," *Science Advances*, Aug. 14, 2015, 1(7):1-9.

Ding, X. et al., "High-throughput nuclear delivery and rapid expression of DNA via mechanical and electrical cell-membrane disruption," *Nature Biomedical Engineering*, Mar. 9, 2017, 1(0039):1-7, Macmillan Publishers Limited, part of Springer Nature.

\* cited by examiner

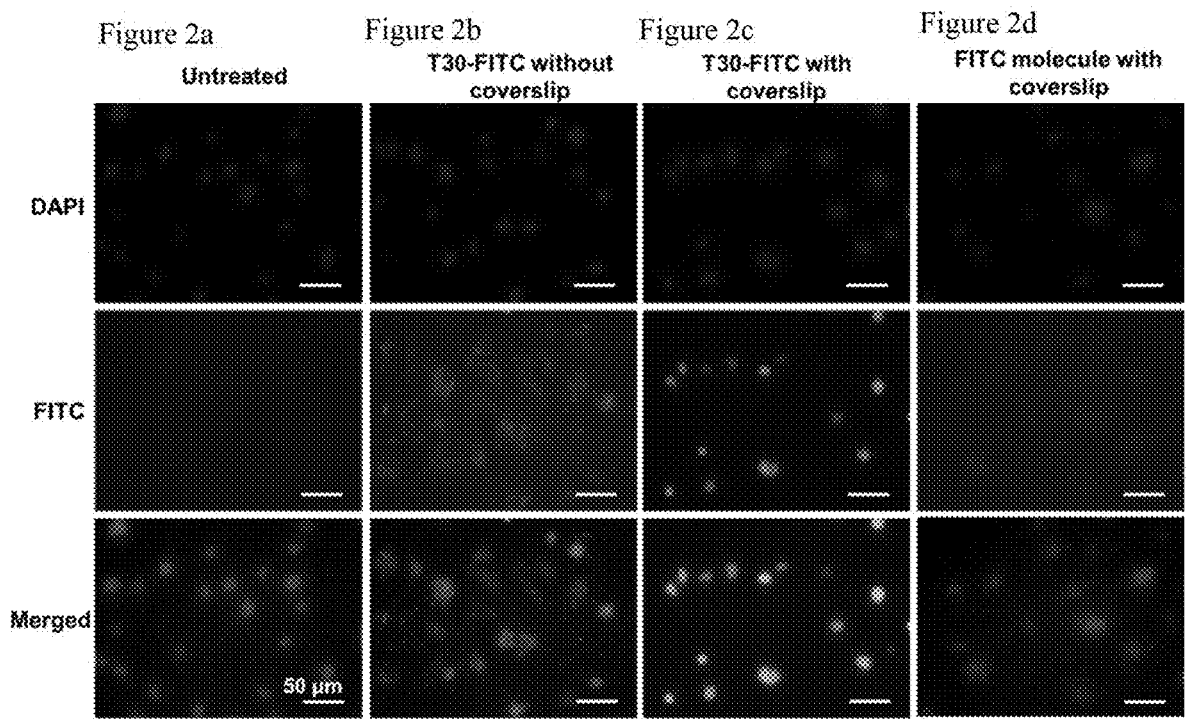

| Compression time (hour) | Cells with Cy3-positive nuclei (%) | Relative MFI of T30-Cy3 (%) | PI-positive cells (%) | MFI of calcein (%) |
|---|---|---|---|---|
| 0 | 0.0 | 0.00 | 0.00 | 100.00 |
| 1 | 35.5 | 81.50±11.56 | 0.69±1.00 | 90.99±9.71 |
| 5 | 53.8 | 100.00±11.92 | 0.00±0.41 | 102.83±5.74 |
| 12 | 49.7 | 128.70±23.35 | 6.35±3.76** | 64.09±5.00** |
| 24 | 80.5 | 225.95±23.32 | 6.86±2.57*** | 61.26±12.50** |

Figure 4a
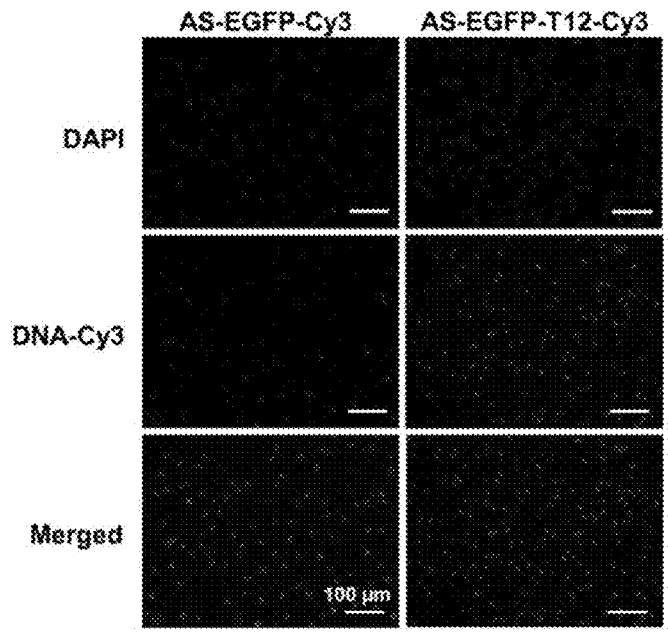
Figure 4b
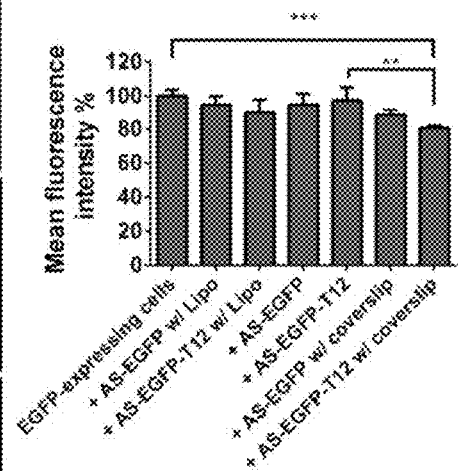
Figure 4c
| Group | Relative MFI of EGFP (%) |
|---|---|
| EGFP | 100.00 ± 3.47 |
| + AS-EGFP w/ Lipo | 94.65 ± 5.16 |
| + AS-EGFP-T12 w/ Lipo | 89.68 ± 8.11 |
| + AS-EGFP | 94.70 ± 6.55 |
| + AS-EGFP-T12 | 97.23 ± 7.74 |
| + AS-EGFP w/ coverslip | 88.40 ± 3.12 |
| + AS-EGFP-T12 w/ coverslip | 80.41 ± 1.34 |

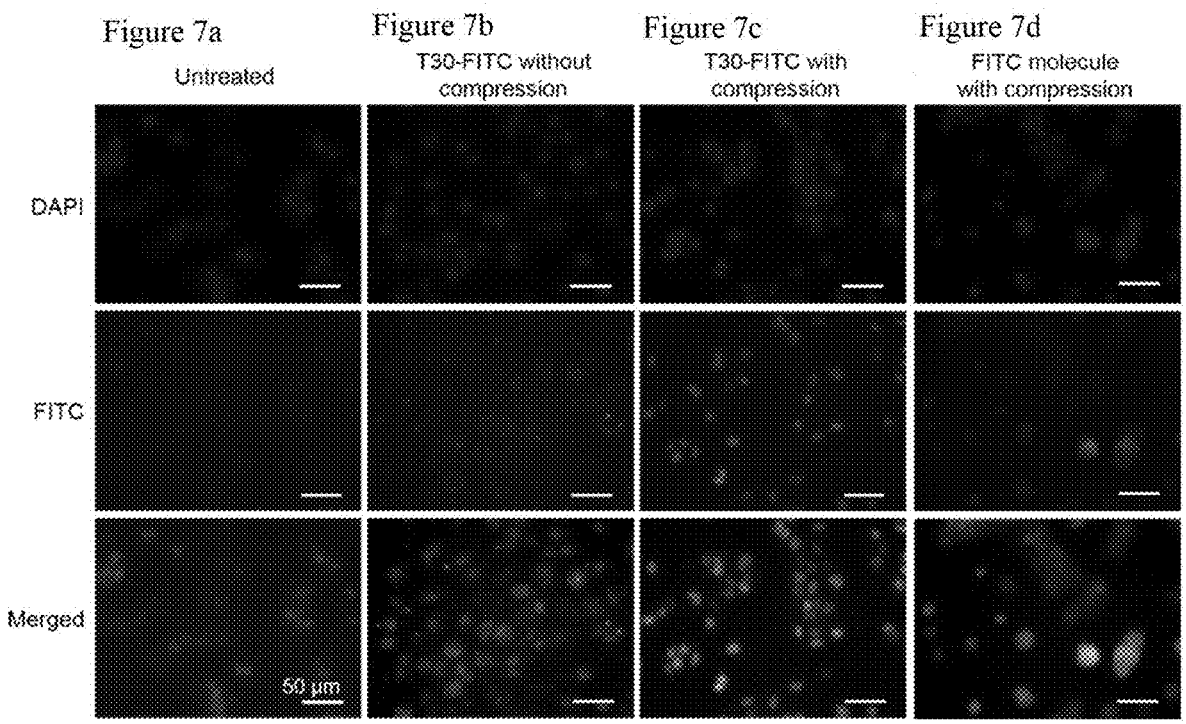
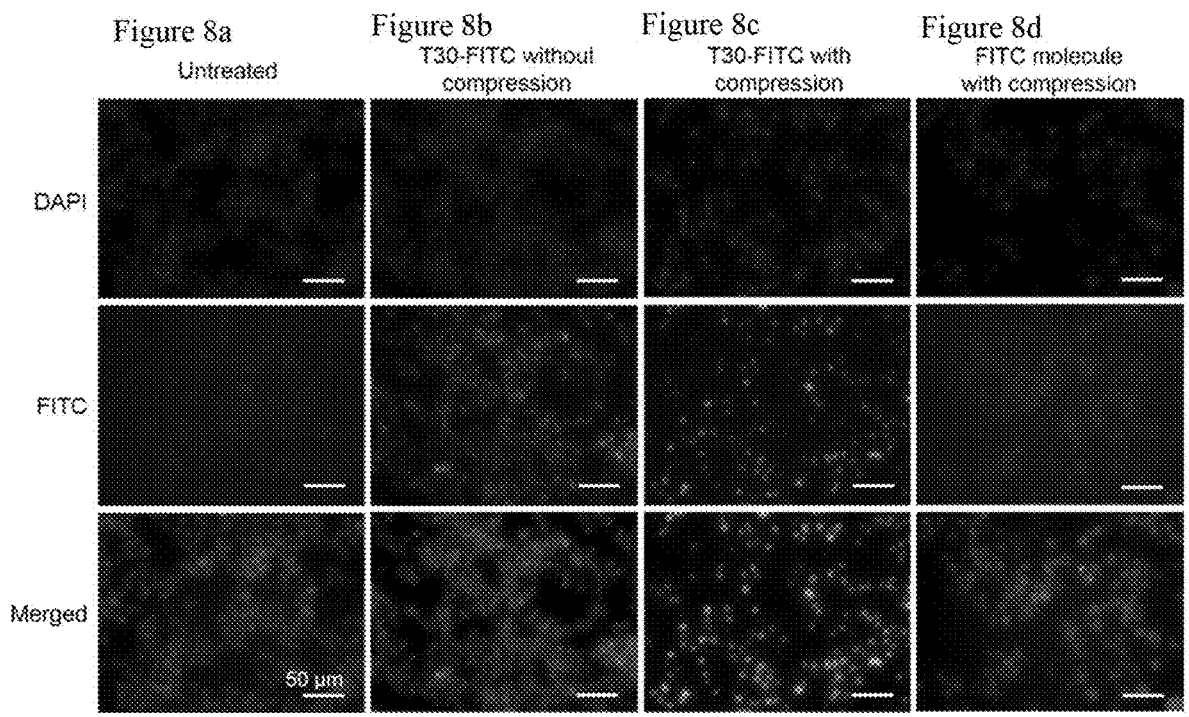

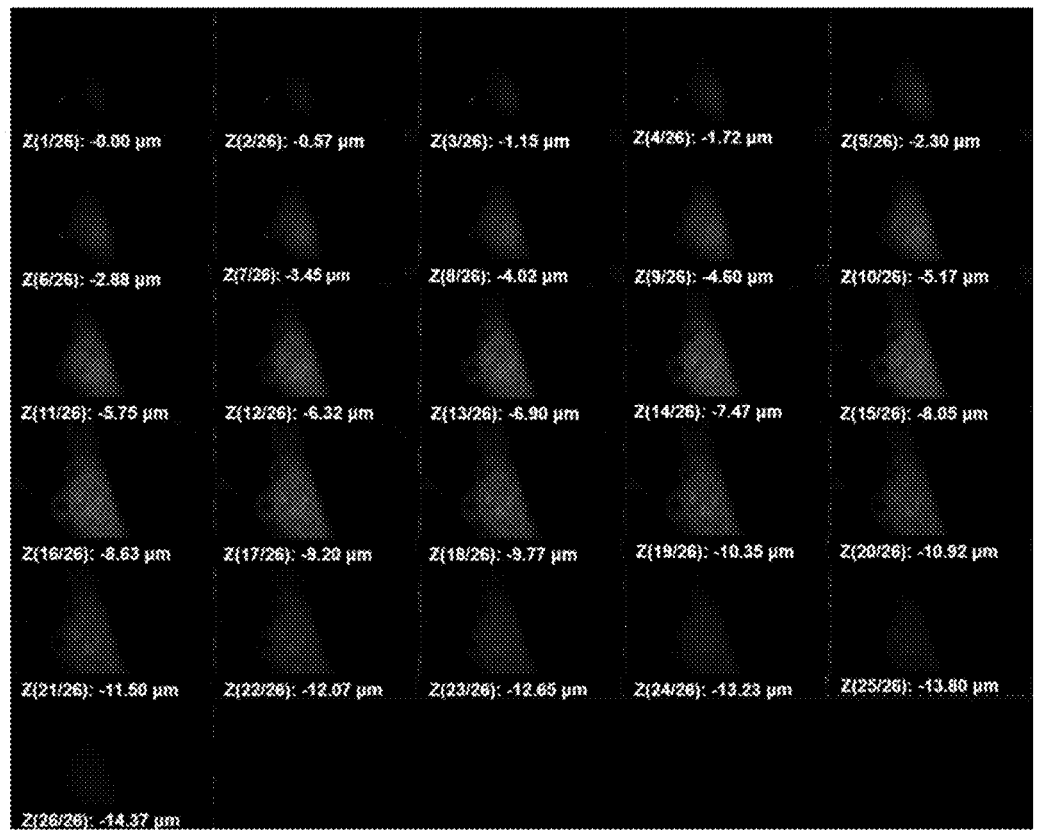
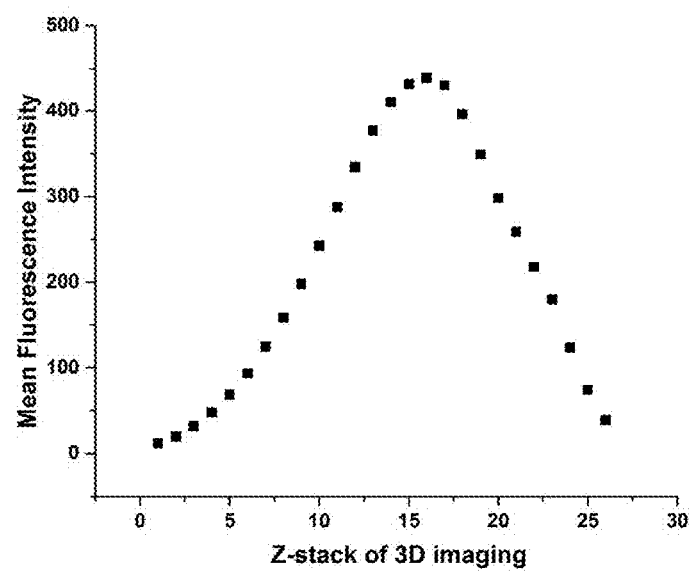
Figure 9

Figure 12a
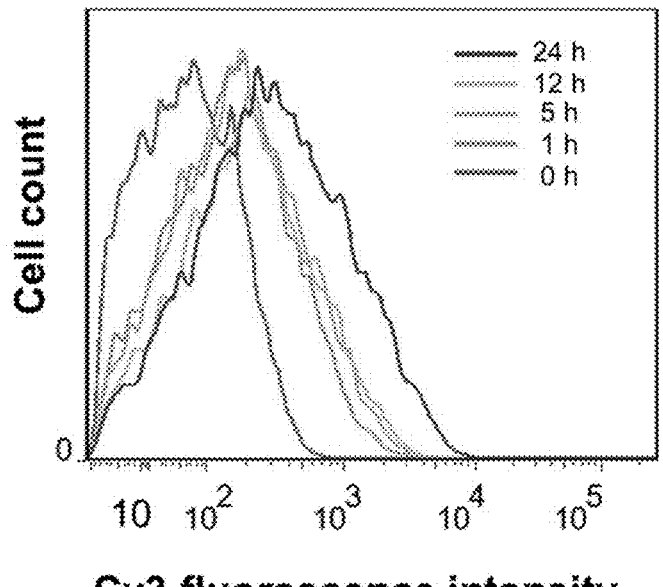
Figure 12b
| Time (h) | Relative Cy3 MFI % |
|---|---|
| 1 | 81.50 ± 11.56 |
| 5 | 100.00 ± 11.92 |
| 12 | 128.70 ± 23.35 |
| 24 | 225.95 ± 23.32 |
Figure 13a
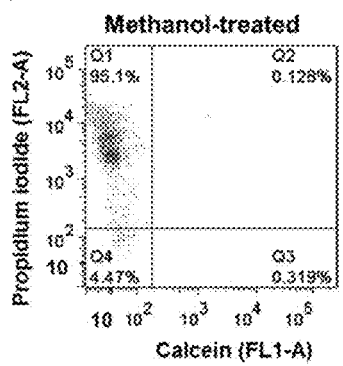
Figure 13b
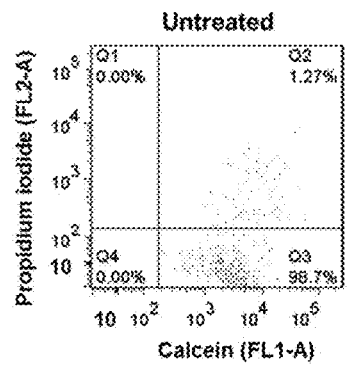
Figure 13c
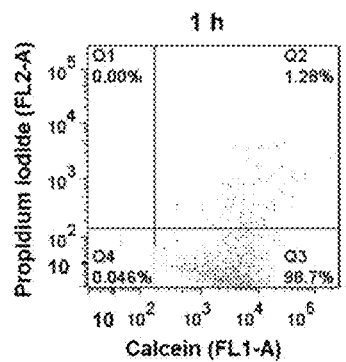
Figure 13d
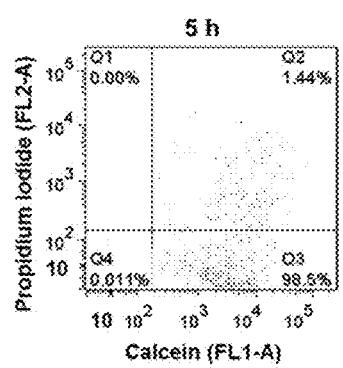
Figure 13e
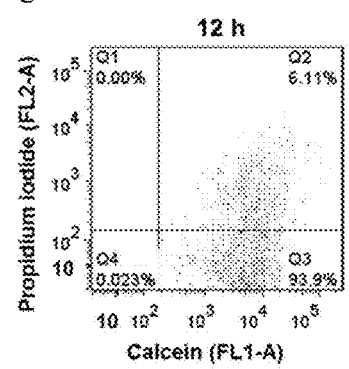
Figure 13f
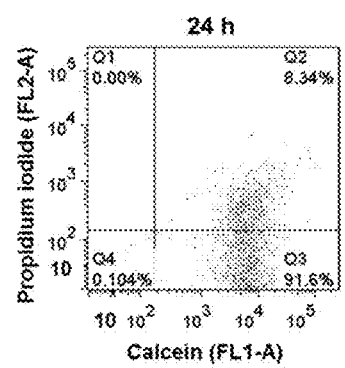

Figure 17a
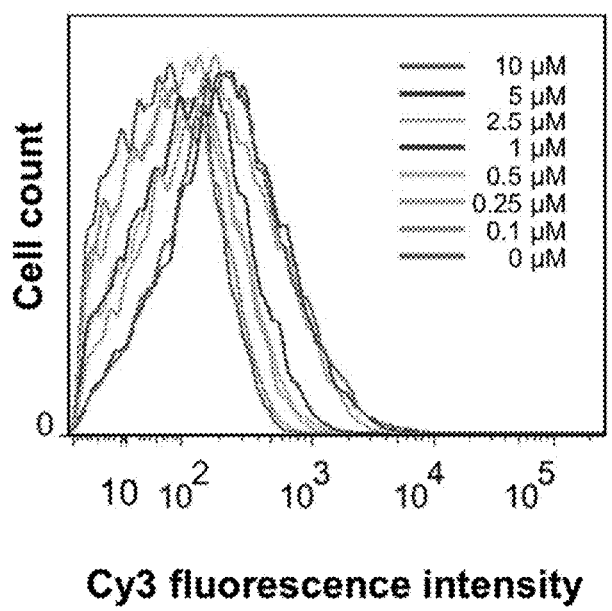
Figure 17b
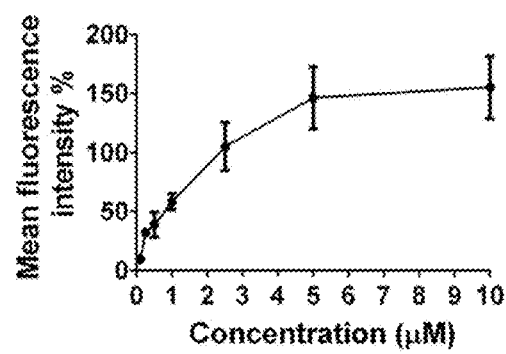
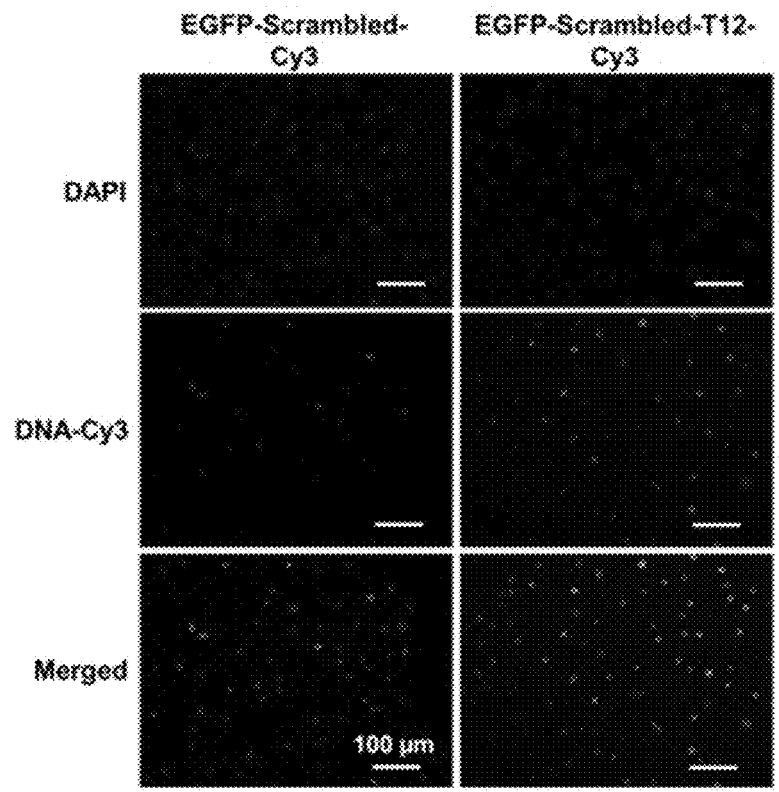
Figure 18

SEQUENCE LISTING

```
<160> NUMBER OF SEQ ID NOS: 8

<210> SEQ ID NO 1
<211> LENGTH: 30
<212> TYPE: DNA
<213> ORGANISM: Artificial
<220> FEATURE:
<223> OTHER INFORMATION: T30-Cy3 oligonucleotide
<220> FEATURE:
<221> NAME/KEY: misc_feature
<222> LOCATION: (30)..(30)
<223> OTHER INFORMATION: 3' end modification: Cyanine 3 (Cy3)

<400> SEQUENCE: 1
tttttttttt tttttttttt tttttttttt                                  30

<210> SEQ ID NO 2
<211> LENGTH: 30
<212> TYPE: DNA
<213> ORGANISM: Artificial
<220> FEATURE:
<223> OTHER INFORMATION: T30-FITC oligonucleotide
<220> FEATURE:
<221> NAME/KEY: misc_feature
<222> LOCATION: (30)..(30)
<223> OTHER INFORMATION: 3' end modification: fluorescein isothiocyanate
      (FITC)

<400> SEQUENCE: 2
tttttttttt tttttttttt tttttttttt                                  30

<210> SEQ ID NO 3
<211> LENGTH: 18
<212> TYPE: DNA
<213> ORGANISM: Artificial
<220> FEATURE:
<223> OTHER INFORMATION: EGFP-Cy3 antisense oligonucleotide
<220> FEATURE:
<221> NAME/KEY: misc_feature
<222> LOCATION: (18)..(18)
<223> OTHER INFORMATION: 3' end modification: Cyanine 3 (Cy3)

<400> SEQUENCE: 3
gagctgcacg ctgccgtc                                               18

<210> SEQ ID NO 4
<211> LENGTH: 30
<212> TYPE: DNA
<213> ORGANISM: Artificial
<220> FEATURE:
<223> OTHER INFORMATION: EGFP-T12-Cy3 antisense oligonucleotide
<220> FEATURE:
<221> NAME/KEY: misc_feature
<222> LOCATION: (30)..(30)
```

```
<223> OTHER INFORMATION: 3' end modification: Cyanine 3 (Cy3)

<400> SEQUENCE: 4
gagctgcacg ctgccgtctt tttttttttt                                    30

<210> SEQ ID NO 5
<211> LENGTH: 18
<212> TYPE: DNA
<213> ORGANISM: Artificial
<220> FEATURE:
<223> OTHER INFORMATION: EGFP antisense oligonucleotide

<400> SEQUENCE: 5
gagctgcacg ctgccgtc                                                 18

<210> SEQ ID NO 6
<211> LENGTH: 30
<212> TYPE: DNA
<213> ORGANISM: Artificial
<220> FEATURE:
<223> OTHER INFORMATION: EGFP-T12 antisense oligonucleotide

<400> SEQUENCE: 6
gagctgcacg ctgccgtctt tttttttttt                                    30

<210> SEQ ID NO 7
<211> LENGTH: 18
<212> TYPE: DNA
<213> ORGANISM: Artificial
<220> FEATURE:
<223> OTHER INFORMATION: EGFP-Scrambled-Cy3  antisense oligonucleotide
<220> FEATURE:
<221> NAME/KEY: misc_feature
<222> LOCATION: (18)..(18)
<223> OTHER INFORMATION: 3' end modification: Cyanine 3 (Cy3)

<400> SEQUENCE: 7
agcgcttcgc accggctg                                                 18

<210> SEQ ID NO 8
<211> LENGTH: 30
<212> TYPE: DNA
<213> ORGANISM: Artificial
<220> FEATURE:
<223> OTHER INFORMATION: EGFP-Scrambled-T12-Cy3 antisense sequence
<220> FEATURE:
<221> NAME/KEY: misc_feature
<222> LOCATION: (30)..(30)
<223> OTHER INFORMATION: 3' end modification: Cyanine 3 (Cy3)

<400> SEQUENCE: 8
agcgcttcgc accggctgtt tttttttttt                                    30
```

HIGHLY SPECIFIC DELIVERY OF POLYNUCLEOTIDES TO THE CELL NUCLEUS VIA COMPRESSION

CROSS-REFERENCE TO RELATED APPLICATIONS

This application claims the priority benefit of U.S. Provisional Application Ser. No. 62/397,173, filed Sep. 20, 2016, which are incorporated herein by reference in their entireties.

BACKGROUND OF THE INVENTION

Delivery of nucleic acids to the cell nucleus not only can support basic investigations into intracellular biological mechanisms[1-3], but also may pave the way for treating diseases by regulating the expression of target genes[4-5]. Intranuclear delivery is challenging due to the need to penetrate through both the cell membrane and nuclear membrane[4-5]. Despite the plethora of methods available for crossing the cell membrane, many of them do not guarantee specific delivery to the nucleus ensuing cellular entry (e.g., electroporation[6], transfection agent[7-8], nanoparticles[9]). Viral vectors are effective for overcoming the nuclear membrane, yet suffer from concerns over cytotoxicity and immune response[10-11]. Non-viral methods usually entail laborious handling (e.g., microinjection[12]), extensive fabrication (e.g., microneedles[13]), or costly conjugation of targeting biomolecules (e.g., nuclear localization peptides[14-15], aptamers[16]).

Investigations into intranuclear delivery of polynucleotides by applying external pressure to cells were scarce and include gene gun[17] and microneedles[18]. Gene gun and microneedles required the application of pressure on the order of $10^4$-$10^5$ Pa, but do not guarantee specific delivery to the nucleus. Another example of specific intranuclear delivery of oligonucleotides entailed the use of fluid pressure: By infusing a saphenous vein with a fluid that contains micromolar concentrations of DNA at 100 mmHg (i.e., 13,300 Pa) for 10 min, the authors observed intranuclear delivery to 60% of the cells in the myocardium ex vivo[19]. Despite the high transfection efficiency, this method involves cannulation and may distort cell morphology. Indeed, applying pressure on the order of $10^2$-$10^3$ Pa to cells may perturb normal cellular functions. Applying a compressive stress of 100 Pa for 10 h can damage 35% of the myoblasts[20]. Exerting a compressive stress of 5.8 mmHg (i.e., 770 Pa) on cancer cells for 16 h will drive their phenotype to become invasive in the tumor microenvironment[21].

BRIEF SUMMARY OF THE INVENTION

This disclosure provides a method for delivering a polynucleotide into a cell, particularly, into the nucleus of the cell. The method for delivering a polynucleotide into a cell comprises contacting the polynucleotide with the cell and applying pressure on the polynucleotide and the cell in a manner that forces the polynucleotide into the cell, and in eukaryotic cells particularly, into the nucleus of the cell. In certain embodiments, the pressure is applied for several hours, for example, about 0.1 hour to 10 hours, and about 4 to 6 hours, at the pressure of about 0.1 Pascal (Pa) to about 50 Pa. Polynucleotides at a concentration of about 0.1 µM to about 100 µM can be used in the methods described herein.

BRIEF DESCRIPTION OF THE DRAWINGS

FIG. 2a shows that untreated bEnd.3 cells do not show much fluorescence signals. (Green: T30-FITC or FITC molecules; Blue: nucleus)

FIG. 2b. Fluorescence images of bEnd.3 cells incubated with T30-FITC for 5 h without coverslip compression. The FITC fluorescent signals are localized in the cytosol but not the nucleus. (Green: T30-FITC or FITC molecules; Blue: nucleus)

FIG. 2c. Fluorescence images of bEnd.3 cells incubated with T30-FITC for 5 h with coverslip compression. The fluorescent signals are predominantly localized in the nucleus. (Green: T30-FITC or FITC molecules; Blue: nucleus)

FIG. 2d shows that incubating bEnd.3 cells with free FITC molecules with coverslip compression for 5 h does not yield appreciable fluorescence signals. (Green: T30-FITC or FITC molecules; Blue: nucleus).

FIG. 4a. Fluorescence images show gene regulation via compression-mediated intranuclear delivery. By compression-mediated delivery, the antisense DNA sequence against the enhanced green fluorescent protein (EGFP) gene (i.e., AS-EGFP-Cy3) can specifically enter the nucleus of bEnd.3 cells in the coverslip periphery. Attaching a T12 segment to its 3' end (i.e., AS-EGFP-T12-Cy3) can enhance its intranuclear delivery by ~90%. (Blue: nucleus; Red: T30-Cy3; Purple: merged).

FIG. 4b shows the mean fluorescence intensity (%). Coverslip-mediated delivery of AS-EGFP-T12 to EGFP-expressing bEnd.3 cells can significantly reduce EGFP expression by ~20%, outperforming Lipofectamine (Lipo)-mediated or gymnotic delivery of the same DNA sequences in terms of EGFP knockdown. Error bar denotes the standard deviation from four independent experiments. P<0.01; *P<0.001.

FIG. 4c shows the quantitation of EGFP knockdown by flow cytometry (see FIG. 4b of the main text for the bar-graph version of the same data with statistical analysis).

Coverslip-mediated delivery of AS-EGFP-T12 significantly reduced EGFP expression in EGFP-expressing bEnd.3 cells by 20%. Strikingly, compression-mediated delivery outperformed Lipofectamine (Lipo)-mediated or gymnotic delivery of the same DNA sequences in terms of EGFP knockdown. Error bar denotes standard deviation from four independent experiments.

Figure 5:
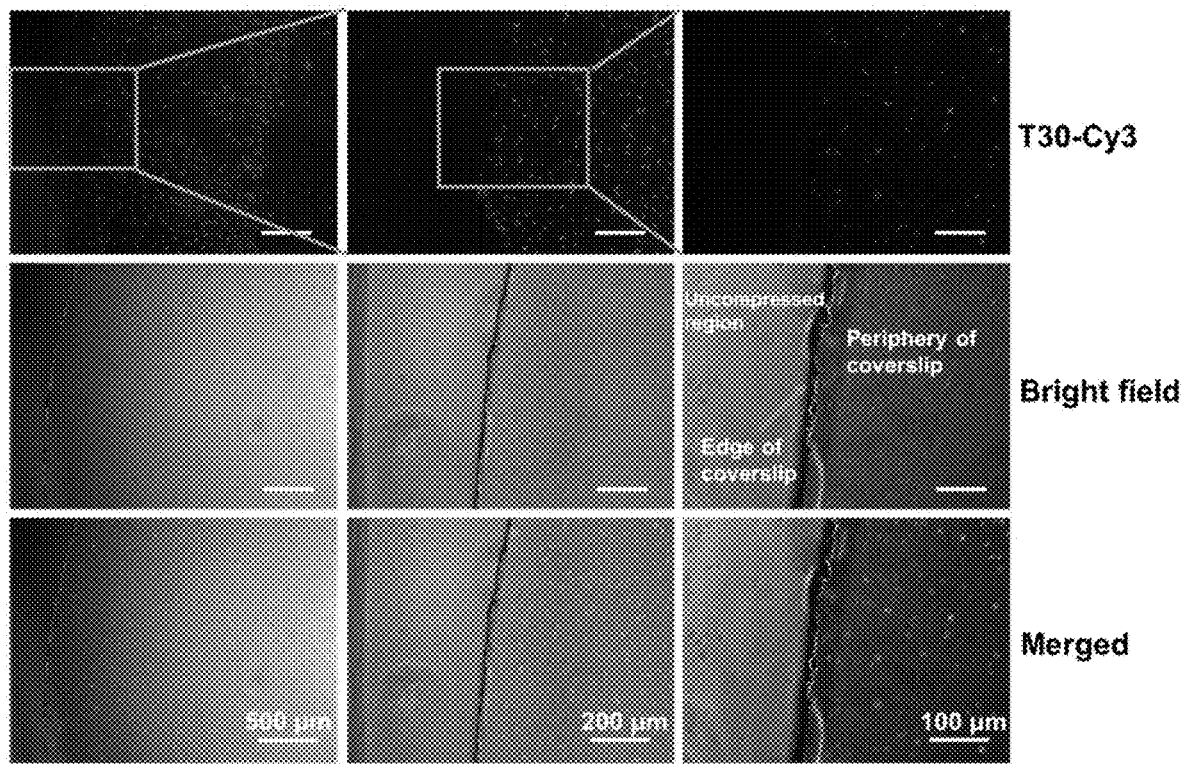

FIG. 5: bEnd.3 cells were incubated with 2.5 µM of T30-Cy3 under coverslip compression for 5 h and subsequently imaged by fluorescence microscopy. Cells in the coverslip periphery exhibited strong Cy3 fluorescence, whereas those in the center do not. The middle column represents the magnified portion of the boxed area in the left column. The right column represents the magnified portion of the boxed area in the middle column. Red=T30-Cy3.

Figure 6:
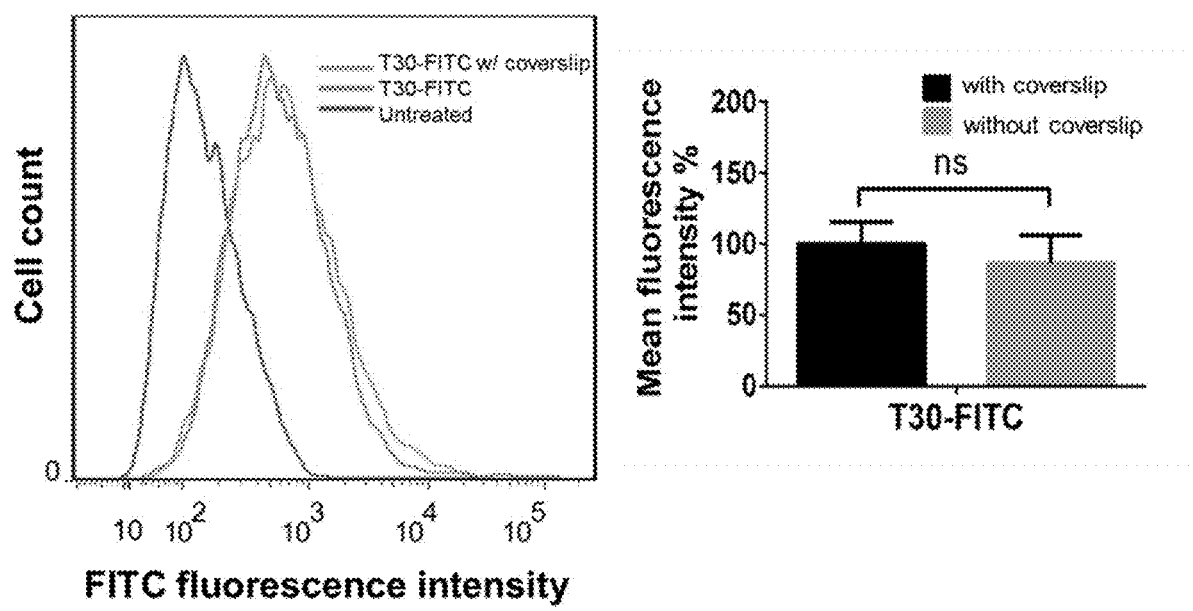

FIG. 6: Incubation of bEnd.3 cells with 2.5 µM of T30-FITC for 5 h under coverslip compression slightly (but not significantly) enhanced the overall cellular uptake of oligonucleotides when compared to cells that are uncompressed by the coverslip, as revealed by flow cytometry measurements. Error bar indicates standard deviation resulting from four independent experiments. MFI %=% mean fluorescence intensity. ns=not significant. Note that 100% MFI refers to the intracellular MFI resulting from a reference study that entails the incubation of bEnd.3 cells with 2.5 µM of T30 for 5 h with coverslip compression.

FIG. 7a shows that untreated Kera-308 cells did not exhibit appreciable fluorescence signals. Blue=DAPI (nucleus).

FIG. 7b shows fluorescence images of Kera-308 cells incubated with T30-FITC without coverslip compression. Kera-308 cells were incubated with 2.5 µM of T30-FITC. After 12 h, significant FITC fluorescence signals (green) were detected in the cytosol. Blue=DAPI (nucleus).

FIG. 7c shows intranuclear delivery of T30-FITC to Kera-308 cells under coverslip compression. By incubating the cells with 2.5 µM of T30-FITC and subjecting them to coverslip compression for 12 h, strong FITC fluorescence signals were observed predominantly in the nuclei for 48.4% of the cells in the coverslip periphery. Note that much accumulation in the cytosol was not observed. Blue=DAPI (nucleus).

FIG. 7d shows fluorescence images of Kera-308 cells with free FITC molecules with coverslip compression. The cells were incubated with free FITC salt at the same FITC concentration as that used in the T30-FITC experiment, followed by coverslip compression for 12 h. Limited intracellular FITC signals were detected without significant accumulation in the nucleus. Blue=DAPI (nucleus).

FIG. 8a shows that untreated RAW264.7 cells did not exhibit appreciable fluorescence signals. Blue=DAPI (nucleus).

FIG. 8b shows fluorescence images of RAW264.7 cells incubated with T30-FITC without coverslip compression. RAW264.7 cells were incubated with 2.5 µM of T30-FITC. After 12 h, significant FITC fluorescence signals (green) were detected in the cytosol. Blue=DAPI (nucleus).

FIG. 8c shows intranuclear delivery of T30-FITC to RAW264.7 cells under coverslip compression. By incubating the cells with 2.5 µM of T30-FITC and subjecting them to coverslip compression for 12 h, strong FITC fluorescence signals were observed predominantly in the nuclei of 63.9% of the cells in the coverslip periphery. Note that much accumulation was not observed in the cytosol. Blue=DAPI (nucleus).

FIG. 8d shows fluorescence images of RAW264.7 cells with free FITC molecules with coverslip compression. The cells were incubated with free FITC salt at the same FITC concentration as that used in the T30-FITC experiment, followed by coverslip compression for 12 h. Limited intracellular FITC signals were detected without significant accumulation in the nucleus. Blue=DAPI (nucleus).

FIG. 9. Intranuclear delivery resolved by three-dimensional (3D) confocal microscopy. Confocal microcopy was used to obtain 3D images of a bEnd.3 cell treated with T30-Cy3 under compression. Cells were seeded in a confocal dish and incubated with 2.5 µM T30-Cy3 under coverslip compression for 5 h. 26 consecutive Z-stack different pictures were collected by optically slicing a whole cell from top to bottom. Cell nucleus (region inside the elliptic nuclear membrane) shows higher fluorescence intensity, implying preferential accumulation of T30-Cy3 inside the nucleus. The cytosol also exhibits some Cy3 fluorescence, albeit at a lower intensity than that inside the cell nucleus. Mean fluorescence intensity measurements of the 26 different Z-stack images show a distribution of Cy3 signals between different layers of the cell.

Figure 10:
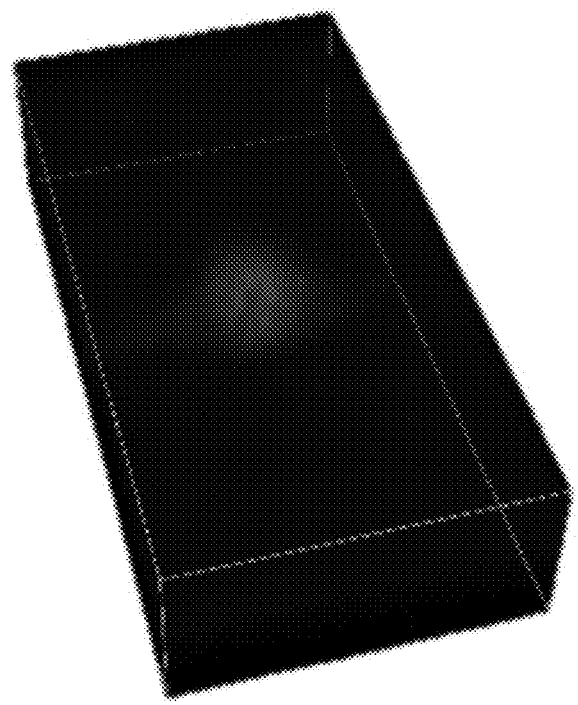

FIG. 10. Intranuclear delivery resolved by 3D reconstruction of confocal images Z-stacks. Based on the same experiment in FIG. 9 mentioned above, we collected additional consecutive Z-stack different pictures by optically slicing through another whole bEnd.3 cell from top to bottom, followed by stitching the Z-stack slices together to form a 3D reconstructed image of the cell. The mean fluorescence intensity of the nucleus is around 6-fold higher than that of the cytosol.

Figures 11A, 11B, 11C:
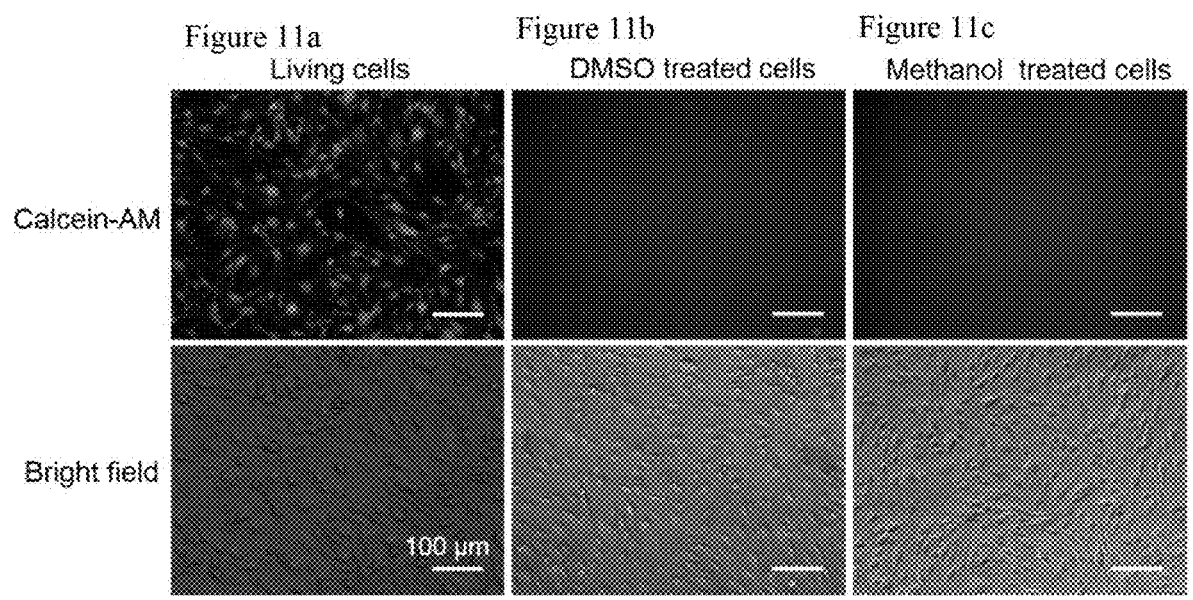

FIG. 11a shows that living bEnd.3 cells manifest bright calcein fluorescence signals due to the acetoxymethyl ester hydrolysis by intracellular esterases (green).

FIG. 11b shows that bEnd.3 cells that were presumably dead upon treatment with absolute DMSO at room temperature for 20 min does not exhibit any detectable calcein fluorescence signals.

FIG. 11c shows that bEnd.3 cells that were presumably dead upon treatment with absolute methanol at room temperature for 20 min does not exhibit any detectable calcein fluorescence signals.

FIG. 12a shows that optimization of compression time for intranuclear delivery. Upon incubation of bEnd.3 cells with 2.5 µM of T30-Cy3 under coverslip compression for different durations of time, flow cytometry was performed to show that the Cy3 mean fluorescence intensity (MFI) of the treated cells increased with compression time.

FIG. 12b shows the relative Cy3 MFI. Error bar indicates standard deviation resulting from four independent experiments. Note that 100% MFI refers to the intracellular MFI resulting from a reference study that entails the incubation of bEnd.3 cells with 2.5 µM of T30 for 5 h with coverslip compression.

FIG. 13a. Representative dual-parameter flow cytometric histogram of Methanol-fixed bEnd.3 cells co-stained with calcein-AM and PI. Methanol-fixed cells were presumably dead and hence detected in Quadrant 1 (Q1: calcein negative, PI positive).

FIG. 13b. Representative dual-parameter flow cytometric histogram of untreated bEnd.3 cells co-stained with calcein-AM and PI. Untreated and uncompressed living cells were detected in Quadrant 3 (Q3: calcein positive, PI negative).

FIG. 13c. Representative dual-parameter flow cytometric histogram of bEnd.3 cells incubated with 2.5 µM of T30 and subjected to coverslip compression for 1 h, and co-stained with calcein-AM and PI. Such cells were primarily detected in Q3 after compression, indicating their overall high viability.

FIG. 13d. Representative dual-parameter flow cytometric histogram of bEnd.3 cells incubated with 2.5 µM of T30 and subjected to coverslip compression for 5 h, and co-stained with calcein-AM and PI. Such cells were primarily detected in Q3 after compression, indicating their overall high viability.

FIG. 13e. Representative dual-parameter flow cytometric histogram of bEnd.3 cells incubated with 2.5 µM of T30 and subjected to coverslip compression for 12 h, and co-stained with calcein-AM and PI. Such cells were primarily detected in Q3 after compression, indicating their overall high viability.

FIG. 13f. Representative dual-parameter flow cytometric histogram of bEnd.3 cells incubated with 2.5 µM of T30 and subjected to coverslip compression for 24 h, and co-stained with calcein-AM and PI.

Such cells were primarily detected in Q3 after compression, indicating their overall high viability. However, as compression continues, a higher percentage of PI-positive cells was detected in Quadrant 2 (Q2: calcein positive, PI positive), which suggests permeabilization of the cell membrane.

Figure 14:
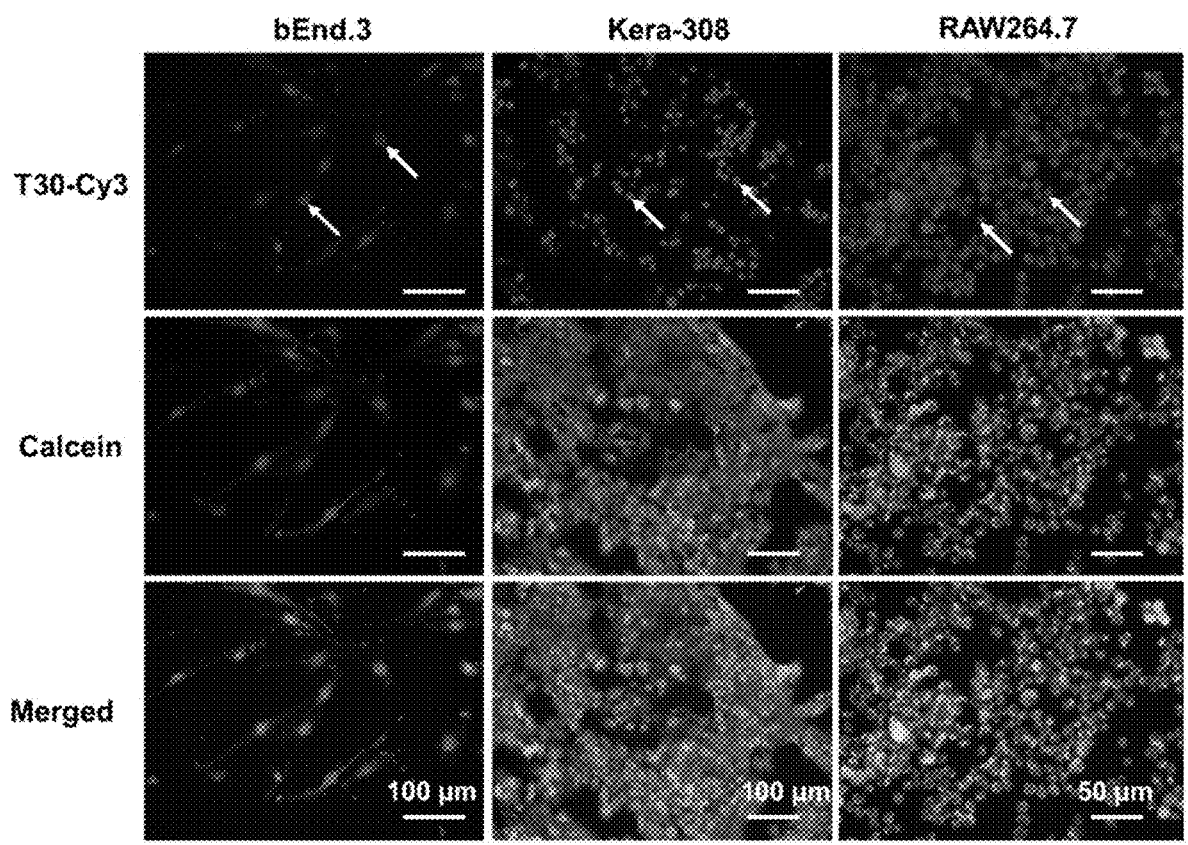

FIG. 14: Different mammalian cell types including bEnd.3, Kera-308, and RAW264.7 were incubated with 2.5 µM of T30-Cy3 and simultaneously subjected to compression by a glass coverslip for 5 h, 12 h, and 12 h respectively. After that, the coverslip was removed, and the compressed cells stained with calcein-AM. Note the predominant accumulation of T30-Cy3 (red) in the nuclei (white arrow) for the three cell types. The cells remain largely viable upon coverslip compression, as evidenced by the intense intracellular calcein fluorescence (green). Thus, compression time may be adjusted to ensure intranuclear delivery of oligonucleotides without inflicting drastic damage to cells.

Figure 15:
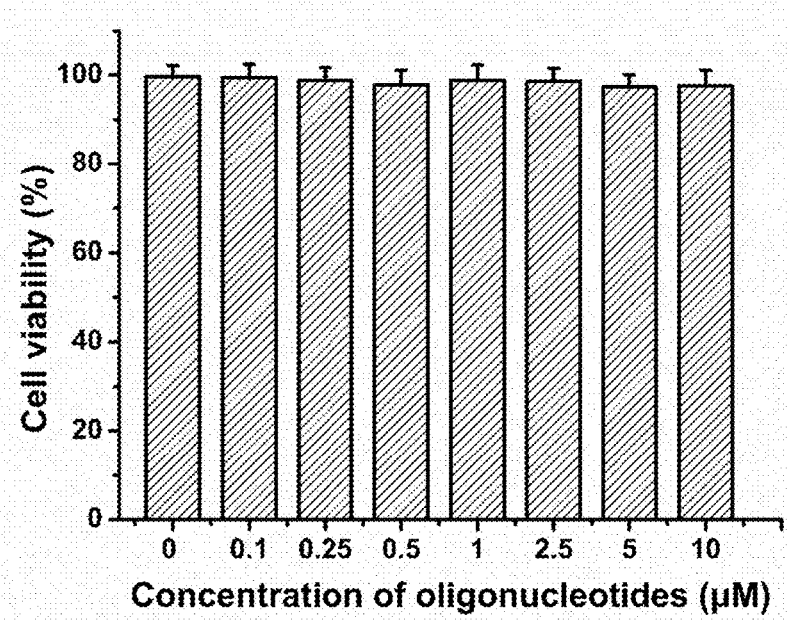

FIG. 15: Upon incubation with T30 DNA in Opti-MEM at varying concentrations in the µM range for 24 h, bEnd.3 cells did not exhibit any apparent loss in metabolic activities by the alamarBlue assay, indicating the compatibility of the DNA polynucleotides with the cell.

Figure 16:
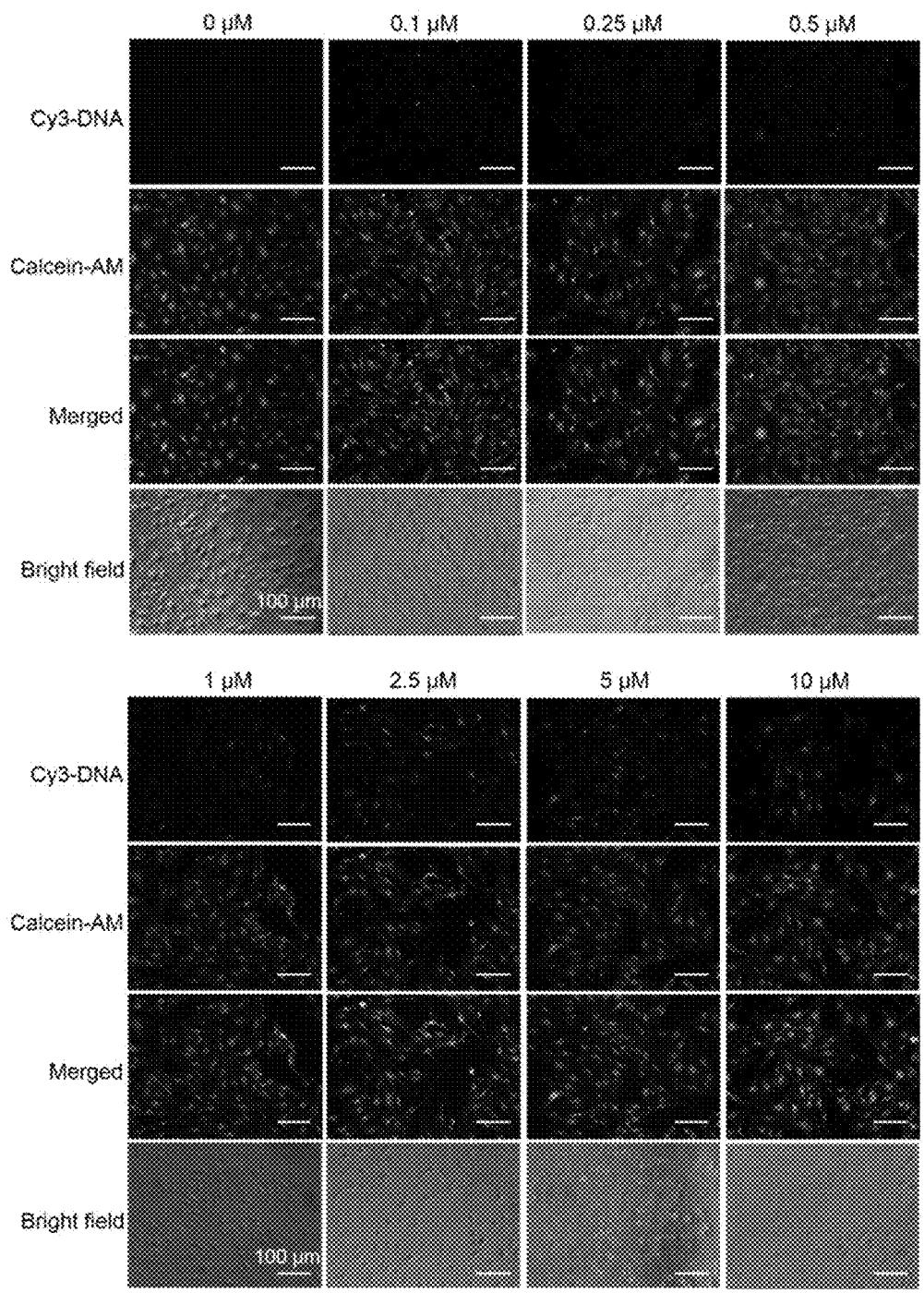

FIG. 16: Optimization of the DNA concentration for nuclear targeting. Upon incubation with T30-Cy3 (red) under coverslip compression for 5 h, bEnd.3 cells did not exhibit appreciable loss in viability, as evidenced by the strong calcein fluorescence signals (green) inside the cell for all T30-Cy3 concentrations tested in the µM range. Incubation of bEnd.3 cells with 2.5 µM of DNA or more resulted in significant delivery to the nucleus.

FIG. 17a shows the optimization of oligonucleotide concentration for intranuclear delivery. Upon incubation of bEnd.3 cells with various concentrations of T30-Cy3 in the micromolar regime under coverslip compression for 5 h, flow cytometry was performed and the Cy3 mean fluorescence intensity (MFI) of the treated cells was observed to increase with concentration.

FIG. 17b shows the relative Cy3 MFI with various concentrations of T30-Cy3. The MFI of cells reached saturation when the incubation concentration was greater than 5 µM, implying no additional delivery of oligonucleotides afforded by compression. Error bar indicates standard deviation resulting from four independent experiments. Note that 100% MFI refers to the intracellular MFI resulting from a reference study that entails the incubation of bEnd.3 cells with 2.5 µM of T30 for 5 h with coverslip compression.

FIG. 18: Upon incubation of bEnd.3 cells with Cy3-containing scrambled EGFP sequences (i.e., EGFP-Scrambled-Cy3) under coverslip compression for 5 h, somewhat limited delivery to the nucleus was observed (24.6% of the cells in the periphery). To the contrary, the bEnd.3 cells treated with Cy3-containing scrambled EGFP sequences with a T12 tail at the 3' end (i.e., EGFP-Scrambled-T12-Cy3) under compression for 5 h exhibit enhanced residency in the nucleus (46.6% of the cells in the periphery). Attachment of a T12 segment to the 3' end of the scrambled EGFP sequence lead to two-fold increase in intranuclear delivery.

Figure 19:
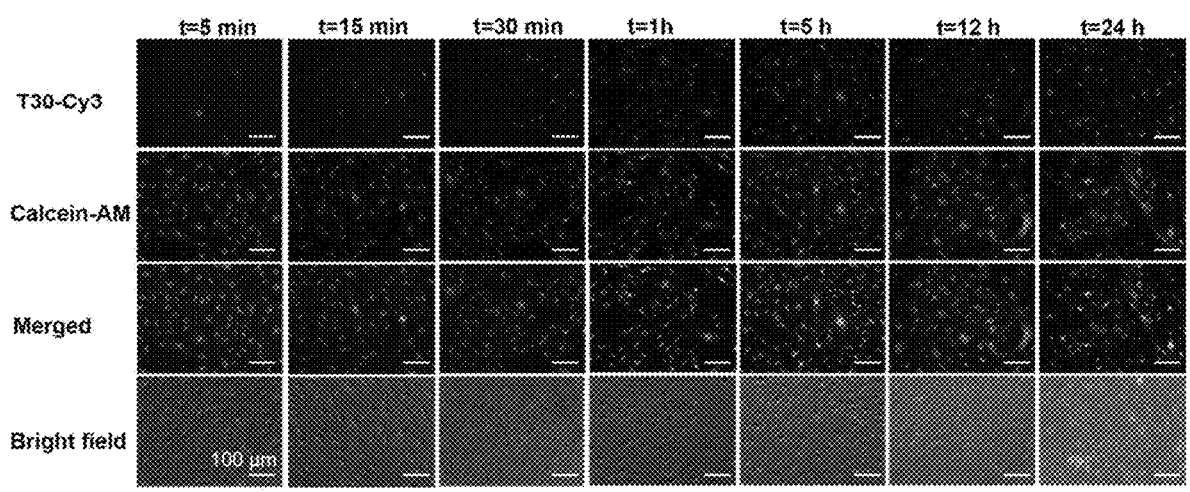

FIG. 19. Intranuclear delivery and cell viability as a function of compression time. bEnd.3 cells were incubated with T30-Cy3 (red) under compression for different durations of time, respectively. Cell viability was indicated by staining the compressed cells with calcein-AM. Compression of bEnd.3 cells for 5 min and 15 min results in some intranuclear delivery of T30-Cy3 while all cells remain viable as indicated by intracellular calcein fluorescence (green). Compression for 30 min, 1 h, or 5 h results in significant intranuclear delivery of T30-Cy3 while no marked cellular damage occurs as indicated by intracellular calcein fluorescence. Compression beyond 12 h gives rise to obvious cellular damage, as seen by the appearance of cells with T30-Cy3 in the nucleus without significant intracellular calcein fluorescence.

Figure 20:
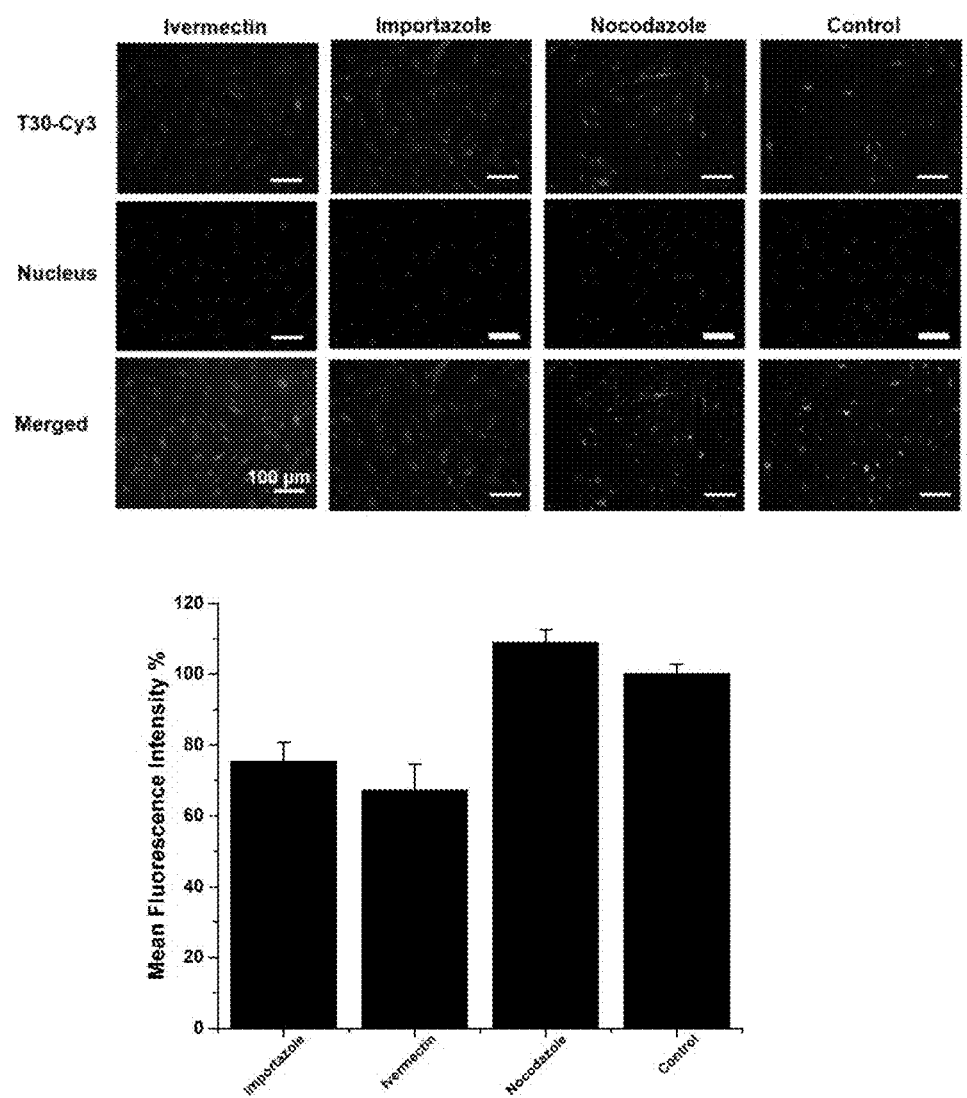

FIG. 20. Pathway for the intranuclear delivery of T30-Cy3 under coverslip compression. bEnd.3 cells were incubated with different inhibitors of nucleus transport pathways, including ivermectin (which inhibits importin α/β-mediated nuclear import), importazole (which blocks importin-β-mediated nuclear import), and nocodazole (which disrupts the formation of microtubules). Error bar indicates standard deviation resulting from four independent experiments. MFI %=% mean fluorescence intensity.

Figure 21:
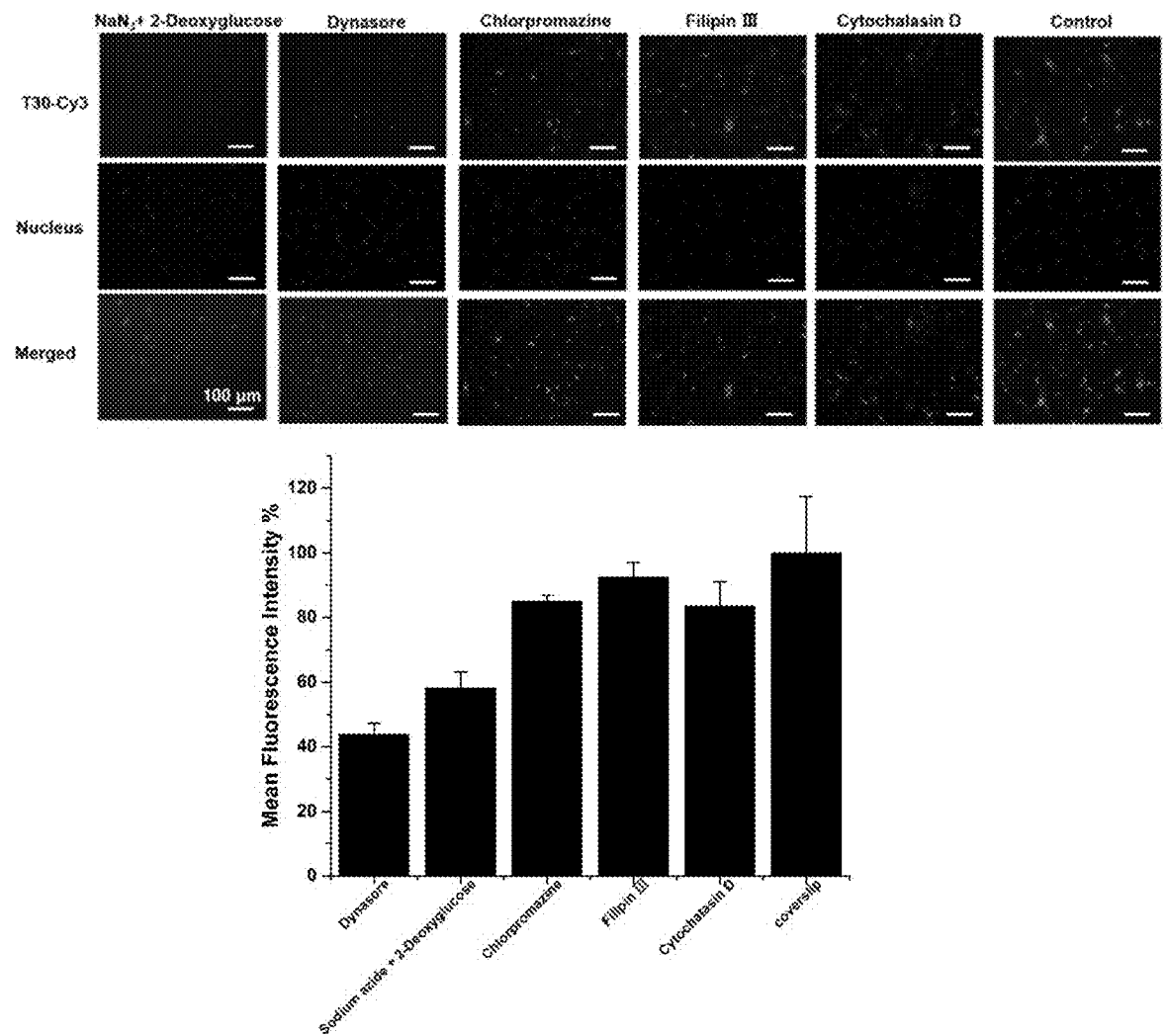

FIG. 21. Pathway for the intracellular entry of T30-Cy3 under coverslip compression. bEnd.3 cells were incubated with a series of pharmacological inhibitors of major cell uptake pathways, including dynasore (which blocks dynamin-mediated uptake), sodium azide in combination with 2-deoxyglucose (which blocks energy-dependent uptake), filipin III (which blocks lipid-raft mediated uptake), and cytochalasin D (which blocks actin-mediated uptake). Error bar indicates standard deviation resulting from four independent experiments. MFI %=% mean fluorescence intensity.

Figure 22:
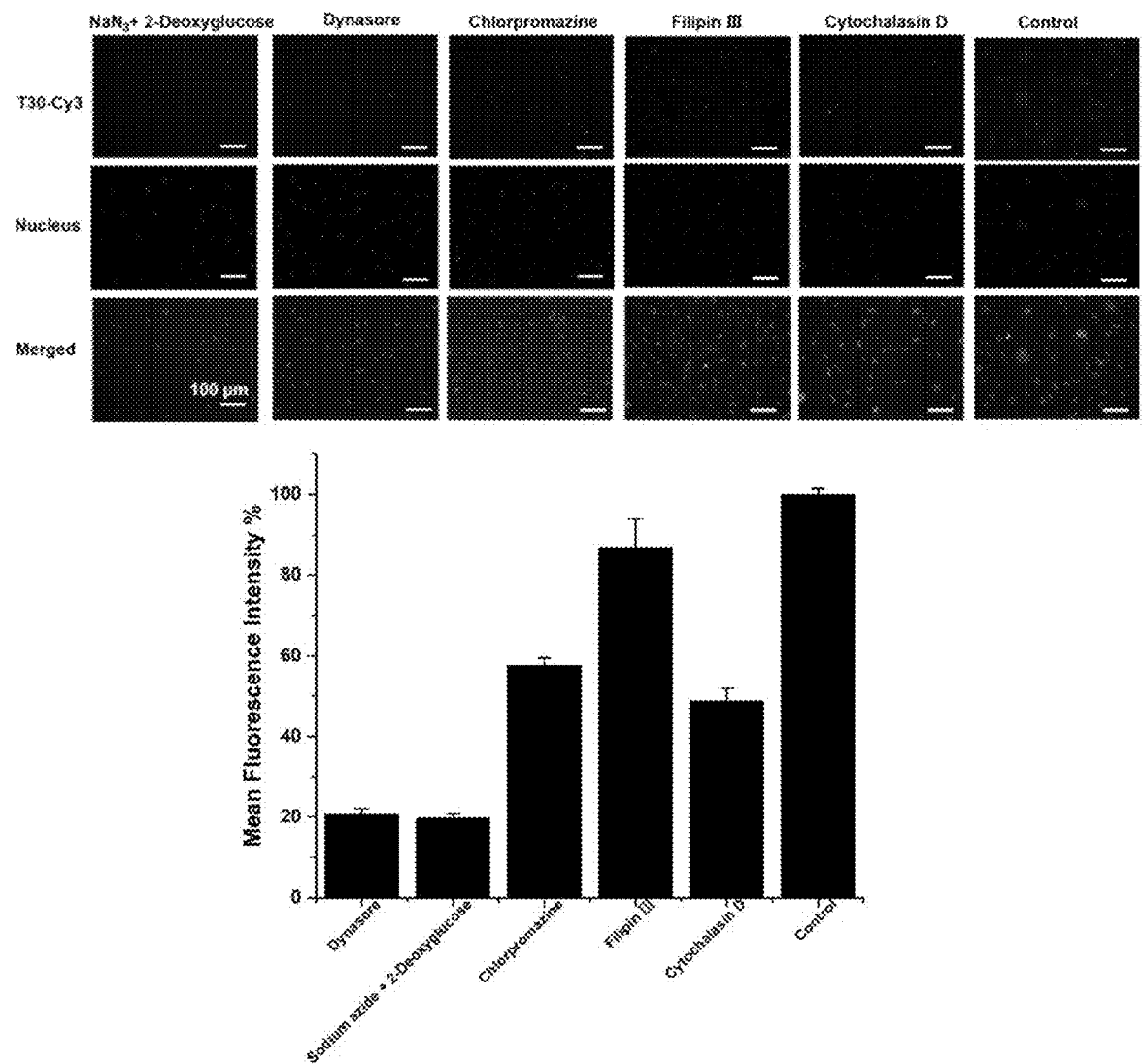

FIG. 22. Pathway for intracellular entry of T30-Cy3 without compression. In the absence of compression, bEnd.3 cells were incubated with T30-Cy3 and a series of pharmacological inhibitors of major cellular uptake pathways, such as dynasore, sodium azide in combination with 2-deoxyglucose, chlorpromazine, filipin III, and cytochalasin D. Error bar indicates standard deviation resulting from four independent experiments. MFI %=% mean fluorescence intensity.

Figure 23:
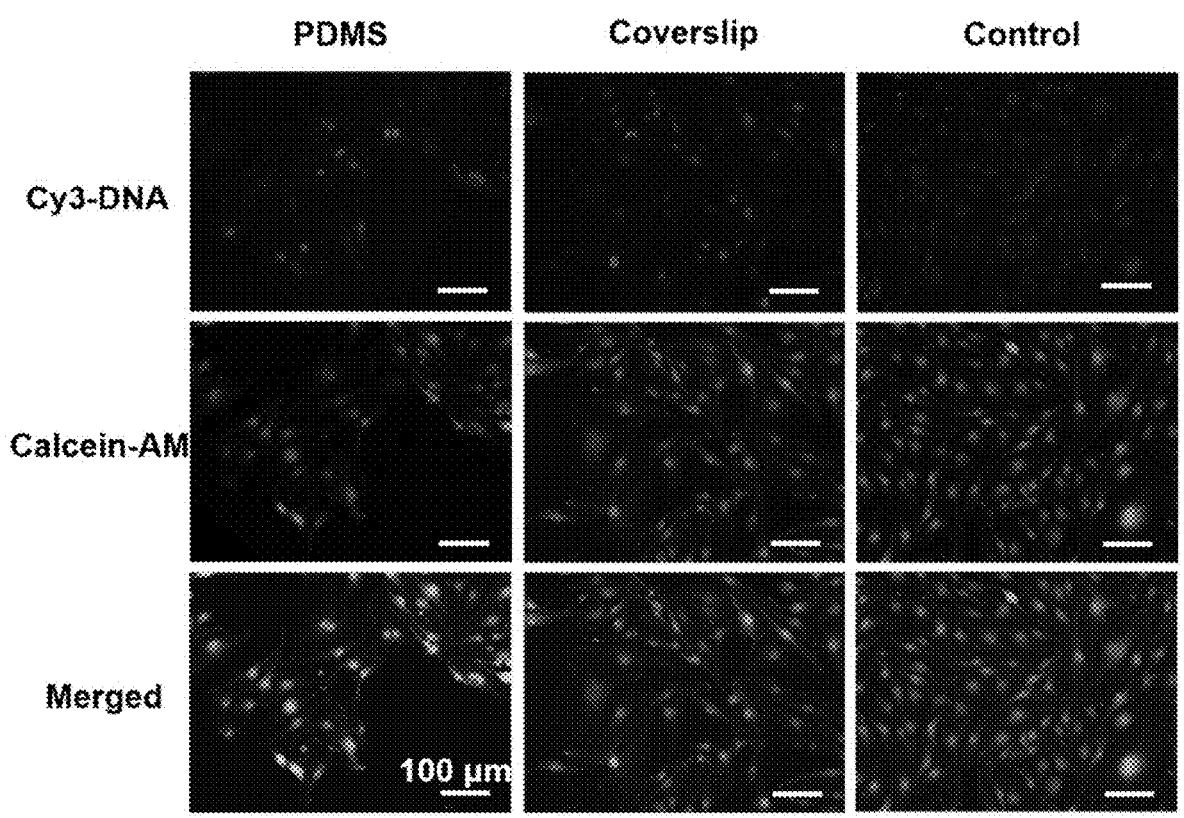

FIG. 23. Dependence of intranuclear delivery of the compressive agent. Polydimethylsiloxane (PDMS) disks of 12 mm in diameter and coverslips were used to apply a compressive stress of ~10 Pa to bEnd.3 cells for 5 h. Similar intranuclear delivery of T30-Cy3 were observed using both compressive agents.

BRIEF DESCRIPTION OF THE SEQUENCES

SEQ ID NO: 1  Oligonucleotide that has thirty thymidines (T30) and contains Cyanine 3 (Cy3) dye at the 3' end
SEQ ID NO: 2  Oligonucleotides that has T30 and contains fluorescein isothiocyanate (FITC) dye at the 3' end -continued

| | |
|---|---|
| SEQ ID NO: 3 | Antisense oligonucleotide that targets the enhanced green fluorescent protein (EGFP) gene and contains a Cy3 molecule at the 3' end |
| SEQ ID NO: 4 | Antisense oligonucleotide that targets EGFP gene and contains twelve thymidines and a Cy3 molecule at the 3' end |
| SEQ ID NO: 5 | 18-base antisense oligonucleotide that targets the EGFP gene |
| SEQ ID NO: 6 | Antisense oligonucleotide that targets EGFP gene and contains twelve thymidines at its 3' end |
| SEQ ID NO: 7 | Scrambled EGFP antisense oligonucleotide that contains Cy3 attached to the 3' end |
| SEQ ID NO: 8 | Scrambled EGFP antisense sequence that contains 12 thymidines and a Cy3 molecule at the 3' end |

DETAILED DISCLOSURE OF THE INVENTION

As used herein, the singular forms "a," "an," and "the" are intended to include the plural forms as well, unless the context clearly indicates otherwise. Further, to the extent that the terms "including," "includes," "having," "has," "with," or variants thereof are used in either the detailed description and/or the claims, such terms are intended to be inclusive in a manner similar to the term "comprising." The transitional terms/phrases (and any grammatical variations thereof) "comprising," "comprises," "comprise," "consisting essentially of," "consists essentially of," "consisting," and "consists" can be used interchangeably.

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 0-20%, 0 to 10%, 0 to 5%, or up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed. In the context of compositions containing amounts of concentrations of ingredients or length of time (duration) or amount of pressure where the term "about" is used, these values include a variation (error range) of 0-10% around the value (X±10%).

To avoid having to set out at length and describe each and every value within the range, the ranges are stated in shorthand in the present disclosure. Any appropriate value within the range can be selected, where appropriate, as the upper value, lower value, or the terminus of the range. For example, a range of 0.1-1.0 represents the terminal values of 0.1 and 1.0, as well as the intermediate values of 0.2, 0.3, 0.4, 0.5, 0.6, 0.7, 0.8, 0.9, and all intermediate ranges encompassed within 0.1-1.0, such as 0.2-0.5, 0.2-0.8, 0.7-1.0, etc.

When ranges are used herein, such as for dose ranges, combinations and subcombinations of ranges (e.g., subranges within the disclosed range), specific embodiments therein are intended to be explicitly included.

The terms "polynucleotide" refers to DNA, RNA, locked nucleic acid (LNA), peptide nucleic acid (PNA), or modified nucleic acids. A polynucleotide can be double-stranded or single-stranded. Modified nucleic acids include polynucleotide comprising chemical backbone modifications that prevent these molecules from degradation by nucleases[25-28]. For example, blunt-ended siRNA molecules with 2'-O-methyl modification are significantly more resistant to plasma derived nucleases than unmodified siRNAs[26]. Additional modifications to nucleic acids are well known to a person of ordinary skill in the art and such embodiments are within the purview of the invention.

For the purpose of this invention, the term "rigid" indicates a material that does not readily bend and maintains its shape and size under pressure, particularly, a pressure below about 100 Pa; more particularly, a pressure below 50 Pa; and even more particularly, a pressure below 20 Pa. Therefore, a "rigid material" as used in this disclosure means a material that requires a pressure of at least 20 Pa before it is deformed.

Figure 1A:
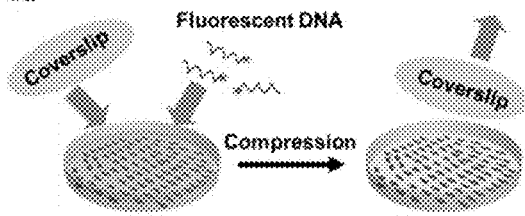
FIG. 1a. Schematic illustration of the experimental setup for intranuclear delivery of oligonucleotides via coverslip compression. Seeded in a 24-well plate, cells are incubated with oligonucleotides under coverslip compression for several hours.

This disclosure provides specific delivery of polynucleotides into a cell, particularly, into the nucleus, by applying mild pressure to cells. The method described herein does not severely compromise cell viability. In one embodiment, a compressive stress on the order of 1-10 Pa is applied to the cells for several hours by placing a solid sheet, for example, a glass coverslip or a sheet of PDMS, over the top of the cell (FIG. 1a).

The method described herein is surprisingly simple for delivering oligonucleotides specifically to the nucleus. In certain embodiments, cells are incubated with oligonucleotides while subjecting them to mild compression, for example, compression afforded by a single glass coverslip. The method takes several hours and does not require the aid of transfection agents and can be applied to different cell types. Compression-mediated intranuclear delivery without drastically compromising cell viability is possible by tuning compression time. Also, knockdown of a target gene is described upon intranuclear delivery of antisense oligonucleotides via coverslip compression. A mild compressive stress on the order of 0.1-50 Pa is sufficient to redirect the trafficking of nucleic acids to intracellular destinations otherwise inaccessible in uncompressed cells. The methods of the invention can be applied for emerging intranuclear applications.

Accordingly, an embodiment of the invention provides a method for delivering a polynucleotide into a cell, particularly, into the nucleus of the cell, the method comprising the steps of:

a) contacting the polynucleotide with the cell, b) applying pressure to the polynucleotide and the cell such that the polynucleotide is forced into the cell, particularly, into the nucleus of the cell.

The cell as used herein can be a prokaryotic or eukaryotic cell. Non-limiting examples of a cell include a bacterial, fungal, plant, algal, protozoan, or animal cell. A fungal cell can be a filamentous fungal cell or yeast cell. Animal cell can be a mammalian or insect cell. Further, a cell can be a cultured cell, for example, cultured in a petri-dish, or present in vivo, for example, a cell of an organ in an animal.

In one embodiment, the subject invention provides a method for delivering a polynucleotide into a nucleus of a target cell, the method comprising the steps of:

a) contacting the polynucleotide with the target cell, b) applying pressure to the polynucleotide and the target cell such that the polynucleotide is forced into the nucleus of the target cell.

According to this disclosure, a lower pressure than used in the prior art, for example, pressure of about 0.1 Pa to about 50 Pa, preferably, about 0.1 Pa to about 10 Pa, is applied on the polynucleotide and the cell. As recognized in the art, 1

Pa pressure corresponds to the pressure of 1 newton per square meter. The disclosure provides that the lower pressure as used in the invention avoids damage to the cells and is effective in delivering the polynucleotide into the cell, particularly, into the nucleus of the cell.

In certain embodiments, the pressure applied to the polynucleotide and the cell in a manner that forces the polynucleotide into the cell is selected from the ranges of: about 0.1 Pa to about 50 Pa; about 1 Pa to about 50 Pa; about 1 Pa to about 45 Pa; about 2 Pa to about 40 Pa; about 3 Pa to about 35 Pa; about 4 Pa to about 30 Pa; about 5 Pa to about 25 Pa; about 6 Pa to about 20 Pa; about 7 Pa to about 15 Pa; and about 8 Pa to about 10 Pa. In a preferred embodiment, the pressure applied to the polynucleotide and the cell in a manner that forces the polynucleotide into the cell is selected from the ranges of: about 0.1 Pa to about 10 Pa; about 2 Pa to about 9 Pa; about 3 Pa to about 8 Pa; about 4 Pa to about 7 Pa; and about 5 Pa to 6 Pa.

In particular embodiments, the pressure is about 1 Pa, about 2 Pa, about 3 Pa, about 4 Pa, about 5 Pa, about 6 Pa, about 7 Pa, about 8 Pa, about 9 Pa, about 10 Pa, about 11 Pa, about 12 Pa, about 13 Pa, about 14 Pa, about 15 Pa, about 16 Pa, about 17 Pa, about 18 Pa, about 19 Pa, about 20 Pa, about 21 Pa, about 22 Pa, about 23 Pa, about 24 Pa, about 25 Pa, about 26 Pa, about 27 Pa, about 28 Pa, about 28 Pa, about 29 Pa, about 30 Pa, about 31 Pa, about 32 Pa, about 33 Pa, about 34 Pa, about 35 Pa, about 36 Pa, about 37 Pa, about 38 Pa, about 39 Pa, about 40 Pa, about 41 Pa, about 42 Pa, about 43 Pa, about 44 Pa, about 45 Pa, about 46 Pa, about 47 Pa, about 48 Pa, about 49 Pa, or about 50 Pa.

In an embodiment, the pressure is applied for a period of about 0.1 hour to about 10 hours. In another embodiment, the pressure is applied for a period selected from the ranges of: about 0.1 hour to about 10 hours; about 0.5 hour to about 10 hours; about 1 hour to about 10 hours; about 2 hours to about 9 hours; about 3 hours to about 8 hours; about 4 hours to about 7 hours; and about 5 hours to about 6 hours. In particular embodiments, the pressure is applied for a period of about: 0.1 hour, 0.5 hour; 1 hour, 2 hours. 3 hours, 4 hours, 5 hours, 6 hours, 7 hours, 8 hours, 9 hours, or 10 hours. In a preferred embodiment, the pressure is applied for a period of about 5 hours.

In one embodiment, the pressure is applied by placing a sheet of solid material onto the cell that is in contact with the polynucleotide and compressing the sheet onto the polynucleotide and the cell in a manner such that the polynucleotide is forced into the cell, particularly, into the nucleus of the cell. In another embodiment, the pressure is applied by placing a sheet of solid material onto the cell and applying a composition, particularly, a solution, comprising the polynucleotide, onto the sheet in a manner that the solution trickles around the sheet and contacts the cells. In one embodiment, the sheet of solid material comprises the composition, particularly a solution, comprising the polynucleotide. In a further embodiment, the pressure is applied by placing the sheet of solid material comprising the polynucleotide onto the cell such that the composition inside the solid trickles through the sheet and contacts the cell.

The sheet can be of any material, preferably, a biocompatible material. In some embodiments, the sheet can be made of rigid material that does not readily bend and maintains its shape and size under pressure. In other embodiments, the sheet can be made of soft material that is not rigid. For example, the soft material includes materials that may be deformed or structurally altered under stress or pressure, particularly pressures below 20 Pa. Accordingly, the sheet can be formed of a metal, glass, plastic, biocompatible polymeric material, or natural material. In a further embodiment, the sheet is made from a porous material that can allow for better fluid immersion and more even distribution of culture medium that facilitates a more even distribution of the culture medium and can avoid accumulation of culture medium towards the periphery of the sheet, for example, the coverslip, without significantly adding to the pressure. In a further embodiment, the sheet is formed of a silicon-based organic polymer, for example, polydimethylsiloxane (PDMS). Additional materials suitable for use in the methods described herein are well known to a person of ordinary skill in the art and such embodiments are within the purview of the invention.

According to the methods described herein, the polynucleotide delivered into a cell is a ribonucleic acid (RNA), deoxyribonucleic acid (DNA), peptide nucleic acid (PNA), locked nucleic acid (LNA), DNA aptamer, antisense DNA, or modified nucleic acid. In certain embodiments, the RNA is a short hairpin RNA (shRNA), a small interfering RNA (siRNA), microRNA, long non-coding RNA, antagoMiR, miRNA sponge, or an antisense RNA (asRNA). A DNA used in the methods of the invention can be single stranded or double stranded. The DNA can contain bases or base pairs ranging from 6 to 10,000. For example, the DNA can contain about 6 bases or base pairs (bp) to about 10,000 bases or bases pairs; about 6 bases or base pairs to about 5000 bases or base pairs; about 6 bases or base pairs to about 2000; and about 6 bases or base pairs to about 1000 bases or base pairs. In other embodiments; the DNA may contain about 20 bases or base pairs to about 10,000 bases or base pairs. A DNA can be a circular DNA or a linear DNA.

In a particular embodiment, the polynucleotide comprises a stretch of thymidine nucleotides (polyT tail) or a stretch of uridine or deoxy-uridine (polyU tail) at the 3' end. PolyT/polyU tail can consist of 5 to 40 nucleotides, particularly, 10 to 25 nucleotides, more particularly, 15 to 20 nucleotides. In specific embodiments, PolyT/polyU tail consists of 12, 15, 20, 25, or 30 nucleotides.

In certain embodiments, the concentration of the polynucleotides contacted with the cell is about 0.1 µM to 100 µM. In certain embodiments, the concentration of the polynucleotides contacted with the cell is selected from the ranges of: about 1 µM to 100 µM; about 2 µM to 95 µM; about 3 µM to 90 µM; about 4 µM to 85 µM, about 5 µM to 80 µM; about 6 µM to 75 µM; about 7 µM to 70 µM; about 8 µM to 65 µM; about 9 µM to 60 µM; about 10 µM to 55 µM, about 11 µM to 50 µM; about 12 µM to 45 µM, about 13 µM to 40 µM; about 14 µM to 35 µM; and about 15 µM to 30 µM. In some embodiments, the concentration of the polynucleotides contacted with the cell is selected from the ranges of: about 1 µM to 90 µM; about 1 µM to 80 µM; about 1 µM to 70 µM; about 1 µM to 60 µM; about 1 µM to 50 µM; about 1 µM to 40 µM; about 1 µM to 30 µM; about 1 µM to 20 µM; and about 1 µM to 10 µM. In other embodiments, the concentration of the polynucleotides contacted with the cell is selected from the ranges of: about 2 µM to about 9 µM; about 3 µM to about 8 µM; about 4 µM to about 7 µM; and about 5 µM to about 6 µM. In particular embodiments, the concentration of the polynucleotides contacted with the cell is about: 1 µM, 2 µM, 3 µM, 4 µM, 5 µM, 6 µM, 7 µM, 8 µM, 9 µM, or 10 µM. In specific embodiments, the concentration of the polynucleotides contacted with the cell is about: 15 µM, 20 µM, 25 µM, 30 µM, 35 µM, 40 µM, 45 µM, 50 µM, 55 µM, 60 µM, 65 µM, 70 µM, 75 µM, 80 µM, 85 µM, 90 µM, 95 µM. or 100 µM. In a preferred embodiment, the concentration of the polynucleotides contacted with the cell is about 2.5 µM or higher than 2.5 µM.

The cell into which a polynucleotide is delivered can be a cultured cell. Accordingly, the methods described herein can be used to deliver a polynucleotide into a cultured cell, for example, in experiments involving cultured cells. In one embodiment, the surface on which a cell is cultured contains grooves. The grooves facilitate a more even distribution of the culture medium and can avoid accumulation of culture medium towards the periphery of the sheet, for example, a coverslip, that is used to apply pressure.

In a further embodiment the cell into which a polynucleotide is delivered is in a live animal, for example, to modulate the expression of a target gene in cells of an organ to treat a disease in the animal. The organ can be skin or an internal organ. An internal organ can be selected from brain, eyes, pineal gland, pituitary gland, thyroid gland, parathyroid glands, heart, lung, esophagus, thymus gland, adrenal glands, appendix, gall bladder, urinary bladder, large intestine, small intestine, kidneys, liver, pancreas, spleen, stoma, ovaries, uterus, testis, skin, and blood. Additional examples of organs and tissues are well known to a person of ordinary skill in the art and such embodiments are within the purview of the invention.

Materials and Methods

Synthesis of Polynucleotides

Standard reagents for the solid-state synthesis of polynucleotides were purchased from Azco Biotech. FITC phosphoramidite and Cy3 phosphoramidite were purchased from Glen Research. All polynucleotides were synthesized by an Oligo-800 Automated Synthesizer (Azco Biotech) and purified by using a high performance liquid chromatography (HPLC) instrument (Agilent 1260) with a Microsorb C18 column (Varian).

Cell Culture

RAW264.7 (mouse macrophage; ATCC), bEnd.3 (mouse brain endothelial; ATCC), and Kera-308 cells (mouse keratinocyte; Cell Lines Service) were routinely cultured in Dulbecco's modified Eagle medium (DMEM; Gibco) supplemented with 10% fetal bovine serum (Gibco) and 1% penicillin-streptomycin (Gibco) at 37° C. in 5% $CO_2$.

Compression-Mediated Intranuclear Delivery

Cells were seeded in 24-well plates (SPL Life Sciences) at a density of $2\times10^5$ cells per well. When the cells reached 70-80% confluency, the serum-containing DMEM was removed, and cells rinsed with phosphate-buffered saline (PBS; pH=7.4) twice. 0.25 mL of DNA polynucleotides (2.5 µM in Opti-MEM) were added to each well. A round coverslip of 12 mm in diameter (Marienfeld Superior), pre-sterilized by sonication in 75% ethanol for 1 h and pre-rinsed with PBS, was immediately placed on top of the cells in each well. Upon different durations of compression, the coverslip and DNA containing-medium were removed, and the cells washed twice with PBS to remove the excess DNA.

Intracellular Location

Cells were fixed with 0.2 mL of 4% paraformaldehyde in PBS for 10 min, rinsed with PBS for three times, and stained with 0.2 mL of 5 µg/mL 4',6-diamidine-2'-phenylindole dihydrochloride (DAPI; Sigma-Aldrich) in PBS for 5 min. The cells were washed with PBS for another three times and observed under a Ti-E Motorized Inverted Fluorescence Microscope (Nikon) with excitation and emission filters of 340-380 nm and 435-485 nm. In general, 150-200 cells in the coverslip periphery were counted and the efficiency of intranuclear delivery was calculated by this formula: [Number of cells with overlapping DNA (Cy3 or FITC) and DAPI signals in the nucleus]÷[Number of cells with DAPI-positive nucleus].

Cell Viability

Cells were incubated with 0.2 mL of calcein-AM working solution (0.5 pig/mL in PBS; Life Technologies) for 10 min at 37° C. After removing the working solution and washing with PBS twice, the cells were imaged by a Ti-E Motorized Inverted Fluorescence Microscope (Nikon). The excitation and emission filters for FITC are 465-495 nm and 515-555 nm. The excitation laser and emission filters for Cy3 are 540/25 nm and 605/55 nm.

Gene Knockdown

Seeded in 24-well plates at a density of $3\times10^5$ cells per well 24 h in advance, bEnd.3 cells were transfected with the pEGFP-N1 plasmid (which contains the enhanced green fluorescent protein (EGFP) gene; Clontech) by Lipofectamine® 2000 (Thermo Fisher Scientific). 24 h after transfection with pEGFP-N1, the cells were divided into different groups and treated with 2.5 µM of antisense DNA oligonucleotides against the EGFP gene (AS-EGFP) or the same sequence with an extra T12 segment (AS-EGFP-T12) formulated in 0.25 mL of Opti-MEM for 5 h, with or without coverslip compression. As a positive control, cells were transfected with 25 nM of antisense oligonucleotides with the aid of 1.5 µL of Lipofectamine® 2000 (also formulated in 0.25 mL of Opti-MEM) for 5 h. Cells were trypsinized, collected by centrifugation at 4,000 rpm for 10 min, resuspended in PBS, and analyzed by a BD FACSVerse flow cytometer. By tuning the forward and side scatter parameters to eliminate dead cells and debris, 10,000 gated events were collected for analysis. The cells were excited at 488 nm, and the fluorescence detected by using a 527/33 nm bandpass filter. Analytical gates were set such that less than 1% of the untreated cells (no EGFP expression) exceeded the gate and fell in the EGFP-positive region. The geometric mean fluorescence intensity of the EGFP-positive region was used to indicate the expression of EGFP in the treated cells compared to the untreated EGFP-expressing cells. The following equation was used to calculate the percentage mean fluorescence intensity (MFI): % MFI=[MFI(treated EGFP-expressing cells)−MFI(untreated wild type cells)]÷[MFI(untreated EGFP-expressing cells)−MFI(untreated wild type cells)]. Data of the MFI after each treatment were analyzed by one-way ANOVA with Tukey post-hoc via GraphPad Prism v5.01.

Cellular Uptake of Oligonucleotides and Flow Cytometry.

Seeded in a 24-well plate, bEnd.3 cells were incubated with different concentrations (e.g., 0.1, 0.25, 0.5, 1, 2.5, 5, or 10 µM) of fluorescently labeled T30 oligonucleotides (e.g., T30-Cy3 or T30-FITC) and compressed by a glass coverslip for different durations of time (e.g., 1, 5, 12, or 24 h). As negative control, cells were either untreated or incubated with the same oligonucleotides but without coverslip compression. After treatment, cells were washed with PBS twice, trypsinized, collected by centrifugation, and resuspended in PBS for analysis by a BD FACSVerse flow cytometer. By tuning the forward and side scatter parameters to eliminate dead cells and debris, we collected 10,000 gated events for analysis. Fluorescence emission was detected at the FL1 channel (527/33 nm) for FITC and the FL2 channel (586/42 nm) for Cy3. Quadruplicate counts were made for each treatment. The mean fluorescence intensity of the fluorophore (i.e., FITC or Cy3) after coverslip compression was compared to the control groups after deducting the background fluorescence of the untreated cells.

Calcein and Propidium Iodide (PI) Co-Staining

Seeded in a 24-well plate, bEnd.3 cells were incubated with 0.25 mL of 2.5 µM of T30 and subjected to coverslip compression for different durations of time. Cells were trypsinized, centrifuged, and re-suspended at a density of $10^6$ cells/mL in PBS containing 0.5 µg/mL calcein-AM (Life Technologies) and 3 µg/mL PI (Sigma Aldrich). After incubation in the dark at 37° C. for 10 min, cells were pelleted again by centrifugation, re-suspended in PBS and kept on ice for flow cytometric analysis. Dead cells were prepared by methanol fixation and co-stained with calcein and PI under the same conditions as control cell samples. For gating, singly stained cells were prepared by incubating PBS-washed and methanol-fixed cells with sole calcein and PI, respectively.

Flow Cytometry

Cells were trypsinized and collected by centrifugation at 4000 rpm for 10 min. They were resuspended in PBS and analyzed by a BD FACSVerse flow cytometer. All cells were analyzed by a BD FACSVerse flow cytometer. By tuning the forward and side scatter parameters to eliminate dead cells and debris, 10,000 gated events were collected for analysis. Fluorescence emission was detected at the FL1 channel (527/33 nm) for calcein and at the FL2 channel (586/42 nm) for PI. Quadruplicate counts were made for each treatment. Cells were analyzed for biparametric histograms FL (calcein) versus FL2 (PI), with single- and double-stained dead cells as controls.

In certain instances, the cells were excited at 488 nm, and the fluorescence was detected by using a 527/33 nm bandpass filter. Analytical gates were set such that less than 1% of the untreated cells (without EGFP expression) exceeded the gate and fell in the GFP-positive region. The geometric mean fluorescence intensity of the GFP-positive region was used to indicate the expression of GFP in the treated cells compared to EGFP-expressing cells that are not treated with antisense polynucleotides. The following equation was used to calculate the percentage mean fluorescence intensity: % MFI=[MFI(treated)−MFI(untreated)]÷[MFI(Group 1)−MFI(untreated)]. Error bars denote standard deviation resulting from four individual experiments. Data of the MFI after each treatment were analyzed by one-way ANOVA with Tukey post-hoc via GraphPad Prism v5.01. *$p<0.05$, $p<0.01$, *$p<0.001$.

Compressive Force Exerted by a Glass Coverslip

A mild compressive stress on the order of 1-10 Pa was exerted to the cells. For a round glass coverslip of 12 mm in diameter and 0.15 mm in thickness, pressure exerted onto the cells simply by placing the glass coverslip on top of cells and incubating with DNA-containing culture medium can be calculated as follows:

$$\sigma_{comp} = \frac{F_{comp}}{\pi R^2} = \frac{\pi R^2 h(\rho_{glass} - \rho_{medium})g}{\pi R^2} =$$
$$(1.5 \times 10^{-4} \text{ m})\left[(2500-1000)\frac{\text{kg}}{\text{m}^3}\right]\left(9.8\ \frac{\text{m}}{\text{s}^2}\right) = 2.2 \text{ Pa}$$

As such, gently placing a glass coverslip onto cells exerts a compressive stress of 2-3 Pa to the cells due to gravity. Additional pressure can be exerted by placing weight onto the glass coverslip.

Figure 1B:
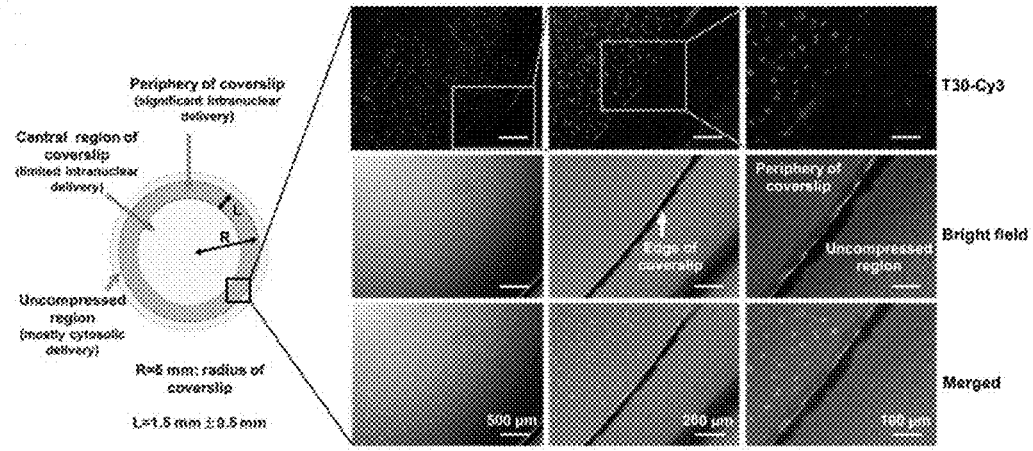
FIG. 1b shows intranuclear delivery of oligonucleotides via coverslip compression. By fluorescence microscopy, the bEnd.3 cells in the periphery (~44% of the area occupied by the coverslip) exhibit strong Cy3 fluorescence, but those in the center do not. (Red: T30-Cy3)

Areal Fraction of Coverslip Periphery with Significant Intranuclear Accumulation of DNA Let R be the radius of a glass coverslip and L be the width of the periphery region of the coverslip that contain cells with significant intranuclear accumulation of DNA owing to compression by the coverslip (FIG. 1b). A round coverslip of 12 mm in diameter is considered (i.e., R=6 mm). Based on the imaging data, the average width of the region is 1.5 mm. The areal fraction of the coverslip periphery, populated by cells whose nuclei contain significant accumulation of oligonucleotides in the periphery, is ~44%. By contrast, cells in the central region of the coverslip (occupying 56% of the total area under compression) do not exhibit significant accumulation in DNA in their nuclei.

$$f_{periphery} = \frac{\pi R^2 - \pi(R-L)^2}{\pi R^2} \times 100\% = \frac{6^2 - (6-1.5)^2}{6^2} \times 100\% = 44\%$$

Cell Viability

In a 96-well plate, bEnd.3 cells were seeded at a density of 60,000 cells per well 24 h in advance. During the experiment, cells were incubated with 0.1 mL of T30 (formulated in Opti-MEM at different concentrations in the µM range) without coverslip compression for 24 h. After removing the DNA and rinsing the cells with PBS twice, the alamarBlue reagent (Invitrogen) was used to test the cell viability according to the manufacturer's instructions by measuring the optical absorbance at 570 nm and 600 nm. Reported data represent mean±SD from four independent experiments.

TABLE 1

List of DNA oligonucleotide sequences

| Name | Sequence (5'→3') | SEQ ID NO: |
|---|---|---|
| T30-Cy3 | TTT TTT TTT TTT TTT TTT TTT TTT TTT TTT Cy3 | 1 |
| T30-FITC | TTT TTT TTT TTT TTT TTT TTT TTT TTT TTT FITC | 7 |
| EGFP-Cy3 | GAG CTG CAC GCT GCC GTC Cy3 | 3 |
| EGFP-T12-Cy3 | GAG CTG CAC GCT GCC GTC TTT TTT TTT TTT Cy3 | 4 |
| EGFP | GAG CTG CAC GCT GCC GTC | 5 |
| EGFP-T12 | GAG CTG CAC GCT GCC GTC TTT TTT TTT | 6 |

TABLE 1-continued

List of DNA oligonucleotide sequences

| Name | Sequence (5'→3') | SEQ ID NO: |
|---|---|---|
| EGFP-Scrambled-Cy3 | AGC GCT TCG CAC CGG CTG Cy3 | 7 |
| EGFP-Scrambled-T12-Cv3 | AGC GCT TCG CAC CGG CTG TTT TTT TTT TTT Cy3 | 8 |

Legend: Cy3 = Cyanine 3; FITC = fluorescein isothiocyanate.

All patents, patent applications, provisional applications, and publications referred to or cited herein are incorporated by reference in their entirety, including all figures and tables, to the extent they are not inconsistent with the explicit teachings of this specification.

Following are examples that illustrate procedures for practicing the invention. These examples should not be construed as limiting. All percentages are by weight and all solvent mixture proportions are by volume unless otherwise noted.

Example 1—Compression Based Delivery of Polynucleotides into Cells

Figure 1C:
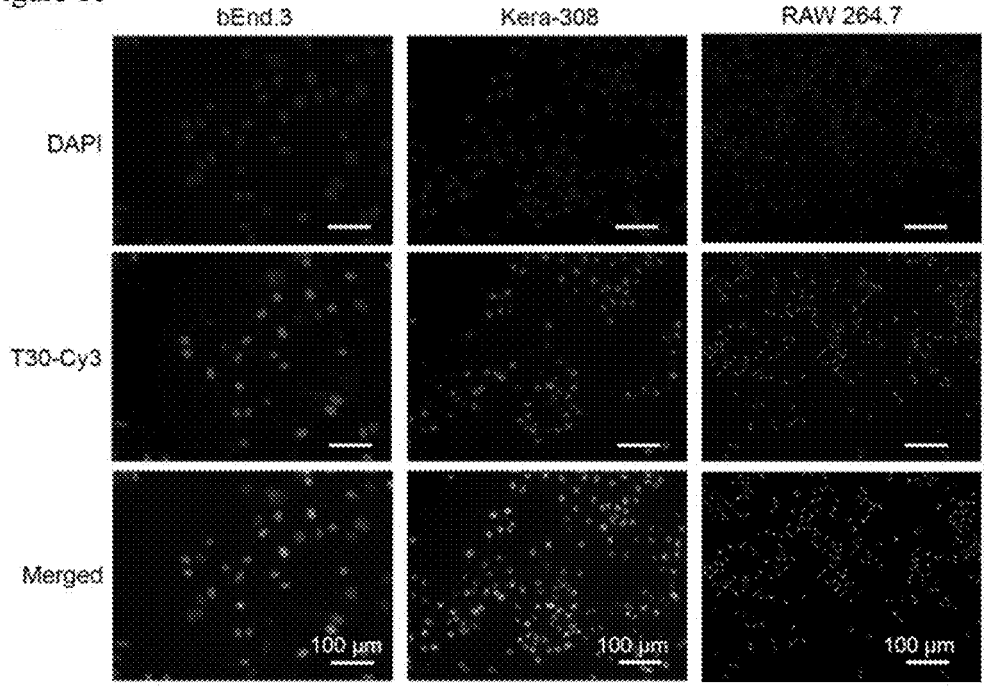
FIG. 1c shows the intranuclear delivery of oligonucleotides via coverslip compression. The coverslip is removed and the compressed cells are stained with DAPI. The Cy3 signals are localized in the nuclei of bEnd.3, Kera-308, and RAW264.7 cells. (Blue: nucleus; Red: T30-Cy3; Purple: merged).

Coverslips are compatible to routine mammalian cell culture procedures and amenable to visualization of the intracellular distribution of nucleic acids by fluorescence microscopy. bEnd.3 (brain endothelial) cells were incubated with 2.5 µM of DNA oligonucleotides that contain 30 repeating thymines (T30) and a Cyanine 3 (Cy3) dye at the 3' end (i.e., T30-Cy3). T30 was selected as a model sequence because T-rich oligonucleotides can be tracked by tracking intracellular RNA by hybridizing to the poly(A) tail. ~30% higher localization of the T-rich oligonucleotides in the nucleus was observed compared to the cytosol[22]. Immediately after adding T30-Cy3 to the cells, a sterile glass coverslip was gently loaded and the cells were subjected to compression by the coverslip for 5 h. Intense Cy3 fluorescence signals were detected by fluorescent microscopy from the compressed cells in the coverslip periphery, which accounted for ~44% of the total area occupied by the coverslip (FIGS. 1b and 5). Cells at the coverslip center were not noticeably fluorescent, probably because the impermeable coverslip restricts their access to the oligonucleotides. Cells uncontacted by the coverslip were weakly fluorescent. To determine the intracellular location of the Cy3 fluorescence, the experiment described above was repeated with minor modifications: After compression, the coverslip was removed, rinsed, the cells were fixed and the cell nuclei were stained with 4',6-diamidino-2-phenylindole (DAPI) (FIG. 1c). Notably, the Cy3 fluorescence was localized to the nucleus but not the cytosol, as evidenced by the overlapping DAPI and Cy3 fluorescence. By manual counting, the Cy3 fluorescence was found in the nuclei of 56.5% of the cells in the coverslip periphery. Moreover, RAW264.7 (macrophage) and Kera-308 (keratinocyte) were incubated cells with T30-Cy3 under coverslip compression for 12 h. Strong Cy3 fluorescence was observed in the nuclei of 43.9% of the Kera-308 cells and 67.8% of the RAW264.7 cells in the coverslip periphery but not the cytosol, a result consistent with the bEnd.3 cells data.

The role of compression on the intranuclear delivery of oligonucleotides (FIGS. 2a-d) was next ascertained. Firstly, bEnd.3 cells were incubated with 2.5 µM of T30 oligonucleotides attached to a fluorescein isothiocyanate (FITC) molecule at the 3' end (i.e., T30-FITC) without applying any compression to the cells. After 5 h, FITC fluorescence was detected in the cytosol but not the nucleus, an observation consistent with past reports on the "gymnotic delivery" oligonucleotides that does not require the aid of transfection agents[23]. In contrast, after incubating bEnd.3 cells with T30-FITC at the same concentration under coverslip compression for 5 h, strong FITC fluorescence was detected in the nuclei of 47.1% of the cells in the coverslip periphery without obvious accumulation in the cytosol, a result consistent with T30-Cy3 imaging data in FIG. 1b. As proved by flow cytometry, the mean fluorescence intensity (MFI) of the compressed cells is only slightly (but not significantly) higher than that of the uncompressed cells upon incubation with T30-FITC or T30-Cy3 at the same concentration (FIG. 6). Thus, coverslip compression only redirects the intracellular destination of T30 from the cytosol to the nucleus; it does not enhance its overall cellular uptake. bEnd.3 cells were also incubated with free FITC molecules (not conjugated to T30) at the same FITC concentration as that used in the T30-FITC experiment. Upon 5 h of compression, weak intracellular fluorescence was detected without any significant intranuclear delivery. Besides bEnd.3 cells, specific delivery of T30-FITC to the nuclei of Kera-308 and RAW264.7 cells was also achieved by subjecting them to coverslip compression for 12 h; T30-FITC predominantly resided in the cytosol (not the nucleus) for the uncompressed Kera-308 and RAW264.7 cells (FIGS. 7a-7d and 8a-8d).

To understand the intracellular localization of the oligonucleotides after coverslip compression, we used confocal microcopy to obtain 3D images of a bEnd.3 cell treated with T30-Cy3 under compression. Cells were seeded in a confocal dish and incubated with 2.5 µM T30-Cy3 under coverslip compression for 5 h. 26 consecutive Z-stack different pictures were collected by optically slicing a whole cell from top to bottom. Cell nucleus (region inside the elliptic nuclear membrane) shows higher fluorescence intensity, implying preferential accumulation of T30-Cy3 inside the nucleus (FIG. 9). The cytosol also exhibits some Cy3 fluorescence, albeit at a lower intensity than that inside the cell nucleus. Mean fluorescence intensity measurements of the 26 different Z-stack images show a distribution of Cy3 signals between different layers of the cell (FIG. 9). Notably, the central slices of the cell exhibit the strongest Cy3 fluorescence.

Based on the same experiment mentioned above, we collected additional consecutive Z-stack different pictures by optically slicing through another whole bEnd.3 cell from top to bottom, followed by stitching the Z-stack slices together to form a 3D reconstructed image of the cell (FIG. 10). The mean fluorescence intensity of the nucleus is around 6-fold higher than that of the cytosol.

Example 2—Optimization of the Compression Time

Figures 3A, 3B:
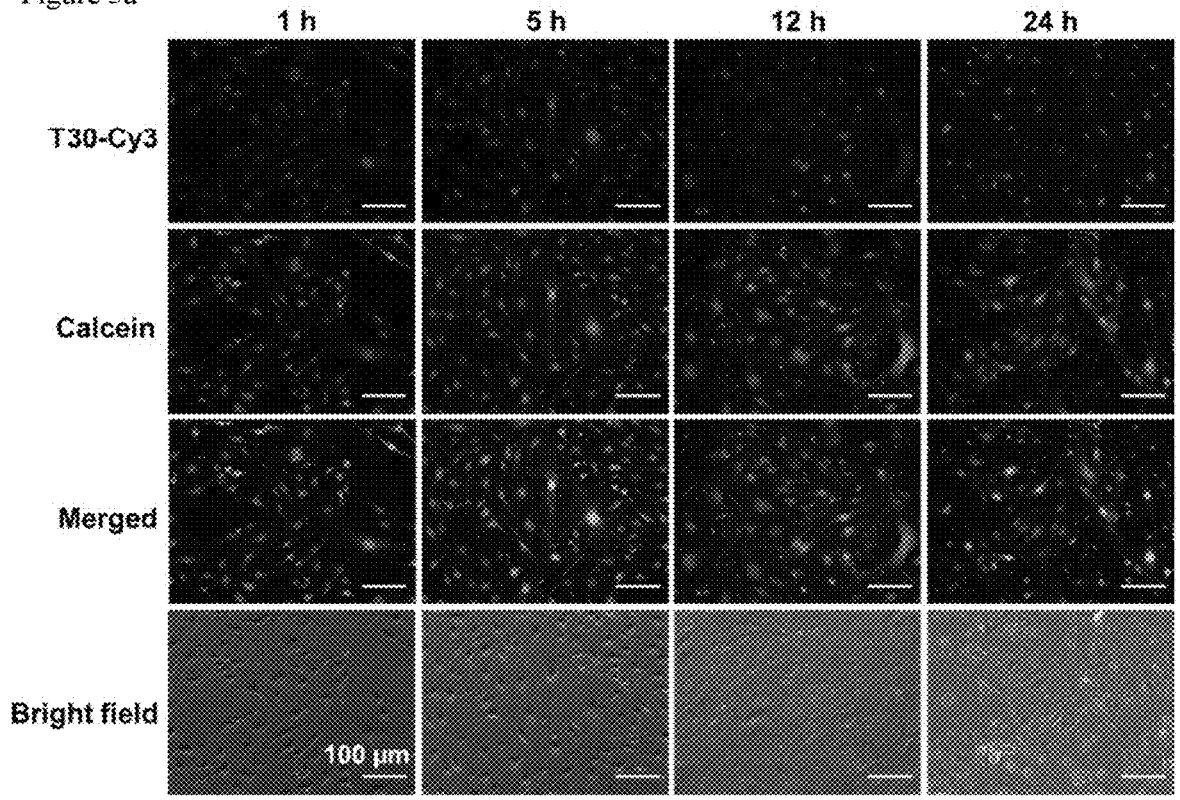
FIG. 3a. Fluorescence images show the efficiency of intranuclear delivery and cell viability. Compression of bEnd.3 cells beyond 12 h gave rise to obvious cellular damage, as seen by the appearance of cells with T30-Cy3 (red) in the nucleus without significant intracellular calcein fluorescence (green).
FIG. 3b shows balancing the efficiency of intranuclear delivery and cell viability. Compression for 5 h led to significant intranuclear delivery without drastically compromising cell viability, as revealed by the emergence of propidium iodide (PI)-positive cells and lack of reduction in calcein fluorescence. Standard deviation results from four independent experiments. 100% "relative mean fluorescence intensity (MFI) of T30-Cy3" refers to the intracellular MFI normalized to that of the 5 h time point. P<0.01; *P<0.001.

The compression time was optimized to balance intranuclear delivery and cell viability, because prolonged compression may cause cellular injury. After incubating bEnd.3 cells with T30-Cy3 under compression for various durations of time, the intracellular distribution of T30-Cy3 was correlated with the viability of the compressed cells by calcein-AM staining (FIGS. 3a-b, and 19). Living cells emit strong calcein fluorescence; however, the cells that are presumably dead upon treatment with organic solvents do not (FIGS. 11a-11c). After coverslip compression for 5 min, we can observe intranuclear entry of T30-Cy3 in several isolated cells. Intranuclear delivery increases as compression time increases. Compression for 30 min results in significant intranuclear delivery of T30-Cy3 while no marked cellular damage occurred as indicated by intracellular calcein fluorescence (FIG. 21). On delivery, the Cy3 fluorescence is localized in the nucleus after 1 h of compression, and continues to persist in the nucleus upon compression till the $24^{th}$ hour. Compression for 5 h gives rise to efficient intranuclear delivery without drastically compromising cell viability. However, compression of bEnd.3 cells beyond 12 h gives rise to obvious cellular damage, as seen by the appearance of cells with T30-Cy3 (red) in the nucleus without significant intracellular calcein fluorescence (FIGS. 3a and 19). By manual counting, the number of cells with Cy3-positive nuclei in the coverslip periphery increased from 32.9% after 1 h of compression to 80.5% after 24 h of compression. By flow cytometry, the Cy3 MFI of the cells beneath the coverslip (including those Cy3-positive cells in the periphery and Cy3-negative cells at the center) increased by ~177% between the $1^{st}$ and $24^{th}$ hour of compression (FIG. 12a-12b). On viability, cells in the coverslip periphery appear viable after 5 h of compression, as revealed by the strong intracellular calcein fluorescence that overlaps with the intense intranuclear Cy3 fluorescence. After 12 h of compression, while most cells exhibit Cy3 and calcein fluorescence, the emergence of cells with intranuclear Cy3 fluorescence was noticed but not intracellular calcein fluorescence. After 24 h of compression, spatial separation of Cy3 and calcein fluorescence was detected: Cells with copious amounts of DNA in the nucleus were injured or dead. To assess the extent of injury, bEnd.3 were incubated with T30 under coverslip compression for various durations of time, followed by co-staining them with calcein-AM and propidium iodide. By flow cytometry, ~40% reduction was detected in the MFI of calcein of the compressed cells (both in the center and periphery) after 12 h of compression; shorter compression durations do not lead to reduction in calcein MFI. Also, cells with positive propidium iodide MFI values were detected after 12 h of compression; shorter compression times yield undetectable fluorescence (FIG. 13a-13f). As such, the optimal compression time for bEnd.3 cells is about 5 h. In Kera-308 and RAW264.7 cells, compression time may be optimized to achieve specific intranuclear delivery without compromising cell viability (FIG. 14). To optimize the oligonucleotide concentration for intranuclear delivery, that incubation of bEnd.3 cells with up to 10 μM of T30 for 24 h was verified not to curb metabolic activities of the cell (FIG. 15). By incubating cells with different concentrations of T30-Cy3 under compression for 5 h, calcein-AM staining was performed to prove that the cells remain largely viable (FIG. 16). Intense Cy3 fluorescence was also observed in the nucleus at concentrations of 2.5 μM or higher. By flow cytometry, the saturation of Cy3 MFI of the cells was noted when the DNA concentration exceeded 5 μM (FIG. 17a-17b). Thus, the optimal concentration for bEnd.3 cells is about 2.5 to 5 μM.

Example 3—Gene Expression Via Compression Based Delivery of Polynucleotides

The potential of the compression-based approach to regulate gene expression was tested. bEnd.3 cells were incubated with one of the two types of DNA polynucleotides while subjecting them to compression for 5 h (FIG. 4a). One type contains an 18-base antisense sequence that targets the enhanced green fluorescent protein (EGFP) gene[24] attached to a Cy3 molecule at its 3' end (denoted EGFP-Cy3). The other type features the same antisense portion with twelve thymidines and a Cy3 molecule attached to its 3' end (denoted EGFP-T12-Cy3). Remarkably, EGFP and EGFP-T12 accumulated in the nuclei of 19.1% and 44.1% of the cells in the coverslip periphery, respectively, which indicates the utility of the T12 segment in promoting intranuclear delivery. Attachment of a T12 segment to the 3' end of a scrambled EGFP sequence also boosted its intranuclear delivery by ~90% (FIG. 18).

Next, EGFP-expressing bEnd.3 cells were transfected with AS-EGFP or AS-EGFP-T12 oligonucleotides by Lipofectamine-mediated and gymnotic delivery for 5 h. As verified by flow cytometry, the T12 segment does not significantly affect the knockdown efficiency of the antisense DNA sequence (FIGS. 4b-4c,). Finally, by transfecting EGFP-expressing bEnd.3 cells with AS-EGFP-T12 under coverslip compression for 5 h, significant reduction was achieved in the expression of EGFP by 20%. This extent of reduction outperforms the reduction attainable by Lipofectamine-mediated (11%) or gymnotic delivery (3%) of the same DNA sequence.

As such, the invention provides coverslip compression as a simple and effective method for delivering nucleic acids specifically to the cell nucleus without severely compromising cell viability. A mild compressive stress on the order of 0.1-10 Pa to cells can redirect to intracellular destinations otherwise inaccessible in uncompressed cells (i.e., from cytosol to nucleus), a result of fundamental interest to cell biologists and technological advance to pharmaceutical science. The compression-mediated polynucleotide delivery method provided herein presents applications in emerging intranuclear technologies like genome editing.

Example 4—Pathway for the Intranuclear and Intracellular Delivery of T30-Cy3

To investigate the pathway for intranuclear delivery, bEnd.3 cells were incubated with different inhibitors of nucleus transport pathways, including ivermectin (which inhibits importin α/β-mediated nuclear import), importazole (which blocks importin-β-mediated nuclear import), and nocodazole (which disrupts the formation of microtubules) (FIG. 20). Upon ivermectin and importzole treatment, the T30-Cy3 accumulates in the cytosol but with limited intranuclear entry, indicating that intranuclear delivery is mediated by the importin α/β-mediated nuclear import pathway. However, treatment with nocodazole does not reduce accumulation of T30-Cy3 in the nucleus, suggesting limited involvement of microtubules.

To investigate the pathway for intracellular delivery under coverslip compression, bEnd.3 cells were incubated with a series of pharmacological inhibitors of major cell uptake pathways, including dynasore (which blocks dynamin-mediated uptake), sodium azide in combination with 2-deoxyglucose (which blocks energy-dependent uptake), filipin III (which blocks lipid-raft mediated uptake), and cytochalasin D (which blocks actin-mediated uptake). By fluorescence microscopy, we observed that T30-Cy3 cannot enter the cytosol and enter the nucleus after treatment by dynasore and sodium azide plus 2-deoxyglucose. By flow cytometry, we observed that the intracellular Cy3 fluorescence decreases sharply by ~60% and ~40%, respectively (FIG. 21), after treatment by dynasore and sodium azide plus 2-deoxyglucose. These results indicate the involvement of dynamin-mediated uptake and energy-dependent uptake under coverslip compression.

In the absence of compression, bEnd.3 cells were incubated with T30-Cy3 and a series of pharmacological inhibitors of major cellular uptake pathways, such as dynasore, sodium azide in combination with 2-deoxyglucose, chlorpromazine, filipin III, and cytochalasin D. Treatment with dynasore, sodium azide plus deoxyglucose can reduce the cellular uptake of T30-Cy3 by 80%, implying strong dependence of dynamin- and energy-mediated endocytosis. Notably, treatment with chlorpromazine and cytochalasin D can also decrease the cellular uptake of T30-Cy3 by 40% and 50%, respectively (FIG. 22), suggesting moderate involvement of a pathway mediated by clathrin and actin. These data are somewhat different than those in FIG. 21, whereby the cells are under compression. Therefore, these results imply that dynamin- and energy-mediated uptake applies to both compressed and uncompressed cases, but involvement of clathrin and actin only applies to the uncompressed case.

Example 5—Dependence of Intranuclear Delivery of the Compressed Agent

To investigate the dependence of intranuclear delivery of the compressive agent, polydimethylsiloxane (PDMS) disks of 12 mm in diameter and coverslips were used to apply a compressive stress of ~10 Pa to bEnd.3 cells for 5 h. By fluorescence microscopy, we observed similar intranuclear delivery of T30-Cy3 when cells are under compression of both PDMS and glass coverslip. (FIG. 23).

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

REFERENCES

1. Phair, R. D. & Misteli, T. High mobility of proteins in the mammalian cell nucleus. *Nature* 404, 604-609 (2000).
2. Boisvert, F. M., van Koningsbruggen, S., Navascués, J. & Lamond, A. I. The multi-functional nucleolus. *Nat. Rev Mol. Cell Biol.* 8, 574-585 (2007).
3. Hornung, V. & Latz, E. Intracellular DNA recognition. *Nat. Rev. Immunol.* 10, 123-130 (2010).
4. Luo, D & Saltzman, W. M. Synthetic DNA systems. *Nat. Biotechnol.* 18, 33-37 (2000).
5. Torchilin, V. P. Recent approaches to intracellular delivery of drugs and DNA and organelle targeting. *Annu. Rev Biomed. Eng.* 8, 343-375 (2006).
6. Potter, H., Weir, L. & Leder, P. Enhancer-dependent expression of human kappa immunoglobulin genes introduced into mouse pre-B lymphocytes by electroporation. *Proc. Natl. Acad. Sci. USA* 81, 7161-7165 (1984).
7. Felgner, P. L. et al. Lipofection: a highly efficient, lipid-mediated DNA-transfection procedure. *Proc. Natl. Acad. Sci. USA* 84, 7413-7417 (1987).
8. Boussif, O. et al. A versatile vector for gene and oligonucleotide transfer into cells in culture and in vivo: polyethylenimine. *Proc. Natl. Acad. Sci. USA* 92, 7297-7301 (1995).
9. Suh, J., Wirtz, D. & Hanes, J. Effective active transport of gene nanocarriers to the cell nucleus. *Proc. Natl. Acad. Sci. USA* 100, 3878-3882 (2003).
10. Crystal, R. G. Transfer of genes to humans: early lessons and obstacles to success. *Science* 270, 404-410 (1995).
11. Tripathy, S. K., Black, H. B., Goldwasser, E. & Leiden, J. M. Immune responses to transgene-encoded proteins limit the stability of gene expression after injection of replication-defective adenovirus vectors. *Nat. Med.* 2, 545-550 (1996).
12. Leonetti, J. P., Mechti, N., Degols, G., Gagnor, C. & Lebleu, B. Intracellular distribution of microinjected antisense oligonucleotides. *Proc. Natl. Acad. Sci. USA* 88, 2702-2706 (1991).
13. Mikszta, J. A., et al. Improved genetic immunization via micromechanical disruption of skin-barrier function and targeted epidermal delivery. *Nat. Med.* 8, 415-419 (2002).
14. Branden, L. J., Mohamed, A. J. & Smith, C. I. E. A peptide nucleic acid-nuclear localization signal fusion that mediates nuclear transport of DNA. *Nat. Biotechnol.* 17, 784-787 (1999).
15. Zanta, M. A., Belguise-Valladier, P. & Behr, J.-P. Gene delivery: A single nuclear localization signal peptide is sufficient to carry DNA to the cell nucleus. *Proc. Natl. Acad. Sci. USA* 96, 91-96 (1999).
16. Dam, D. H. M., et al. Direct observation of nanoparticle-cancer cell nucleus interactions. *ACS Nano* 6, 3318-3326 (2012).
17. O'Brien, J. A. & Lummis, S. C. R. Biolistic transfection of neuronal cultures using a hand-held gene gun. *Nat. Protoc.* 1, 977-981 (2006).
18. McAllister, D. V., Allen, M. G. & Prausnitz, M. R. Microfabricated microneedles for gene and drug delivery. *Annu. Rev. Biomed. Eng.* 2, 289-313 (2000).
19. Mann, M. J., et al. Pressure-mediated oligonucleotide transfection of rat and human cardiovascular tissues. *Proc. Natl. Acad. Sci. USA* 96, 6411-6416 (1999).
20. Yao, Y., Lacroix, D. & Mak, A. F. T. Effects of oxidative stress-induced changes in the actin cytoskeletal structure on myoblast damage under compressive stress: confocal-based cell-specific finite element analysis. Biomech. Model Mechanbiol. DOI: 10.1007/s10237-016-0779-0 (2016).
21. Tse, J. M., et al. Mechanical compression drives cancer cell towards invasive phenotype. *Proc. Natl. Acad. Sci. USA* 109, 911-916 (2012).
22. Politz, J. C., Taneja, K. L. & Singer, R. H. Characterization of hybridization between synthetic oligodeoxynuclotides and RNA in living cells. *Nucleic Acids Res.* 23, 4946-4953 (1995).
23. Stein, C. A. et al. Efficient gene silencing by delivery of locked nucleic acid antisense oligonucleotides, unassisted by transfection reagents. *Nucleic Acids Res.* 38, e3 (2010).

24. Rosi, N. L. et al. Oligonucleotide-modified gold nanoparticles for intracellular gene regulation. *Science* 312, 1027-1030 (2006).
25. Chiu, Y. L. and Rana, T. M. (2002) RNAi in human cells: basic structural and functional features of small interfering RNA. Mol Cell, 10, 549-561.
26. Czauderna, F., Fechtner, M., Dames, S., Aygun, H., Klippel, A., Pronk, G. J., Giese, K. and Kaufmann, J. (2003) Structural variations and stabilising modifications of synthetic siRNAs in mammalian cells. Nucleic Acids Res, 31, 2705-2716.
27. Morrissey, D. V., Lockridge, J. A., Shaw, L., Blanchard, K., Jensen, K., Breen, W., Hartsough, K., Machemer, L., Radka, S., Jadhav, V., Vaish, N., Zinnen, S., Vargeese, C., Bowman, K., Shaffer, C. S., Jeffs, L. B., Judge, A., MacLachlan, I. and Polisky, B. (2005) Potent and persistent in vivo anti-HBV activity of chemically modified siRNAs. Nat Biotechnol, 23, 1002-1007.
28. Soutschek, J., Akinc, A., Bramlage, B., Charisse, K., Constien, R., Donoghue, M., Elbashir, S., Geick, A., Hadwiger, P., Harborth, J., John, M., Kesavan, V., Lavine, G., Pandey, R. K., Racie, T., Rajeev, K. G., Rohl, I., Toudjarska, I., Wang, G., Wuschko, S., Bumcrot, D., Koteliansky, V., Limmer, S., Manoharan, M. and Vornlocher, H. P. (2004) Therapeutic silencing of an endogenous gene by systemic administration of modified siRNAs. Nature, 432, 173-178.

We claim:

1. A method for delivering a polynucleotide into a cell and/or a nucleus of a cell, the method comprising:
   a) contacting the polynucleotide with the cell,
   b) applying pressure of about 0.1 pascal (Pa) to about 50 Pa on the polynucleotide and the cell by a sheet of a solid material such that the polynucleotide is forced into the cell and/or the nucleus of the cell,
   wherein the polynucleotide comprises a stretch of thymidine nucleotides (polyTtail) at least 5 nucleotides long or a stretch of uridine or deoxy-uridine (polyUtail) at least 5 nucleotides long at the 3' or 5' end.

2. The method of claim 1, wherein the pressure is applied by:
   a) placing a sheet of solid material onto the cell that is in contact with the polynucleotide and compressing the sheet onto the polynucleotide and the cell such that the polynucleotide is forced into the cell and/or the nucleus of the cell; or
   b) placing the sheet of solid material onto the cell and applying a composition comprising the polynucleotide onto the sheet such that the composition trickles around the sheet and contacts the cell.

3. The method of claim 1, wherein the pressure is about 1 Pa to about 50 Pa.

4. The method of claim 3, wherein the pressure is selected from the ranges of: about 1 Pa to about 50 Pa; about 1 Pa to about 45 Pa; about 2 Pa to about 40 Pa; about 3 Pa to about 35 Pa; about 4 Pa to about 30 Pa; about 5 Pa to about 25 Pa; about 6 Pa to about 20 Pa; about 7 Pa to about 15 Pa, and about 8 Pa to about 10 Pa.

5. The method of claim 3, wherein the pressure is: 1 Pa, 2 Pa, 3 Pa, 4 Pa, 5 Pa, 6 Pa, 7 Pa, 8 Pa, 9 Pa, 10 Pa, 11 Pa, 12 Pa, 13 Pa, 14 Pa, 15 Pa, 16 Pa, 17 Pa, 18 Pa, 19 Pa, 20 Pa, 21 Pa, 22 Pa, 23 Pa, 24 Pa, 25 Pa, 26 Pa, 27 Pa, 28 Pa, 29 Pa, 30 Pa, 31 Pa, 32 Pa, 33 Pa, 34 Pa, 35 Pa, 36 Pa, 37 Pa, 38 Pa, 39 Pa, 40 Pa, 41 Pa, 42 Pa, 43 Pa, 44 Pa, 45 Pa, 46 Pa, 47 Pa, 48 Pa, 49 Pa, or 50 Pa.

6. The method of claim 1, wherein the cell is a cultured cell.

7. The method of claim 1, wherein the polynucleotide is a ribonucleic acid (RNA), deoxyribonucleic acid (DNA), peptide nucleic acid, locked nucleic acid, DNA aptamer, antisense DNA, or modified nucleic acid.

8. The method of claim 7, wherein the polynucleotide is RNA and the RNA is a short hairpin RNA, small interfering RNA, microRNA, long non-coding RNA, antagoMiR, miRNA sponge, or antisense RNA.

9. The method of claim 7, wherein the polynucleotide is DNA and the DNA is single stranded or double stranded.

10. The method of claim 9, wherein the DNA is about 6 bases or bp to about 1000 bases or bp.

11. The method of claim 1, wherein the PolyT/polyU tail consists of 5 to 40 nucleotides.

12. The method of claim 11, wherein the PolyT/polyU tail consists of 12, 15, 20, 25, or 30 nucleotides.

13. The method of claim 1, wherein the polynucleotide is contacted with the cell at a concentration of about 1 µM to about 100 µM.

14. The method of claim 13, wherein the polynucleotide is contacted with the cell at a concentration selected from the ranges of: about 1 µM to 90 µM; about 1 µM to 80 µM; about 1 µM to 70 µM; about 1 µM to 60 µM; about 1 µM to 50 µM; about 1 µM to 40 µM; about 1 µM to 30 µM; about 1 µM to 20 µM; about 1 µM to 10 µM; about 2 µM to about 9 µM; about 3 µM to about 8 µM; about 4 µM to about 7 µM; and about 5 µM to about 6 µM.

15. The method of claim 13, wherein the polynucleotide is contacted with the cell at a concentration of at least 2.5 µM.

16. The method of claim 1, wherein the pressure is applied for a period of about 0.1 hour to about 10 hours.

17. The method of claim 16, wherein the pressure is applied for a period selected from the ranges of: about 0.5 hour to about 10 hours; about 1 hour to about 10 hours; about 2 hours to about 9 hours; about 3 hours to about 8 hours; about 4 hours to about 7 hours; and about 5 hours to about 6 hours.

18. The method of claim 16, wherein the pressure is applied for about 5 hours.

19. The method of claim 1, wherein the polynucleotide is forced into the cell via a pathway involving dynamin-mediated uptake and energy-dependent uptake and/or the polynucleotide is forced into the nucleus of the cell via the importin α/β-mediated nuclear import pathway, wherein the cell is a brain cell.

* * * * *

UNITED STATES PATENT AND TRADEMARK OFFICE
CERTIFICATE OF CORRECTION

| | | |
|---|---|---|
| PATENT NO. | : 10,533,189 B2 | Page 1 of 1 |
| APPLICATION NO. | : 15/708810 | |
| DATED | : January 14, 2020 | |
| INVENTOR(S) | : Chung Hang Jonathan Choi et al. | |

It is certified that error appears in the above-identified patent and that said Letters Patent is hereby corrected as shown below:

In the Specification

Column 14,
Table 1 (Column 3, Row 2), "7" should read --2--.

Signed and Sealed this
Ninth Day of June, 2020

Andrei Iancu
*Director of the United States Patent and Trademark Office*